(12) United States Patent
Popejoy et al.

(10) Patent No.: US 10,857,001 B2
(45) Date of Patent: Dec. 8, 2020

(54) BONE GRAFT DELIVERY LOADING ASSEMBLY

(71) Applicant: Stryker European Operations Holdings LLC, Kalamazoo, MI (US)

(72) Inventors: Spencer Popejoy, Ringwood, NJ (US); Joshua Stein, Montvale, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 56 days.

(21) Appl. No.: 16/267,492

(22) Filed: Feb. 5, 2019

(65) Prior Publication Data
US 2019/0167443 A1 Jun. 6, 2019

Related U.S. Application Data

(63) Continuation of application No. 15/241,339, filed on Aug. 19, 2016, now Pat. No. 10,231,846.

(51) Int. Cl.
*A61F 2/46* (2006.01)
*A61B 17/70* (2006.01)
*A61B 17/88* (2006.01)

(52) U.S. Cl.
CPC ........ *A61F 2/4601* (2013.01); *A61B 17/7094* (2013.01); *A61B 17/8822* (2013.01); *A61B 17/8833* (2013.01); *A61F 2002/4635* (2013.01)

(58) Field of Classification Search
CPC .......................... A61F 2/4601; A61B 17/7094
See application file for complete search history.

(56) References Cited

U.S. PATENT DOCUMENTS

| 4,994,065 A | 2/1991 | Gibbs et al. |
| 5,015,101 A | 5/1991 | Draenert |

(Continued)

FOREIGN PATENT DOCUMENTS

| EP | 1614403 A1 * | 1/2006 | ......... A61B 17/8822 |
| EP | 1614403 A1 | 1/2006 | |

(Continued)

OTHER PUBLICATIONS

Extended European Search Report including the Written Opinion for Application No. EP 19176555.1 dated Jul. 18, 2019, 7 pages.

(Continued)

*Primary Examiner* — Christian A Sevilla
(74) *Attorney, Agent, or Firm* — Lerner, David, Littenberg, Krumholz & Mentlik, LLP

(57) ABSTRACT

A bone graft loading system includes a loading funnel, syringe, cannula, plunger, and loading tool. The loading funnel includes an interior passageway to receive the cannula and a syringe docking portion. The syringe may be coupled to the syringe docking portion so that it extends along a longitudinal axis that is transverse to the longitudinal axes of the cannula and the loading funnel. A user may advance bone graft from the syringe to a holding area of the loading funnel. The user may then move the loading tool through the holding area and into the interior space of the cannula to load the cannula with bone graft. This process may be repeated until the cannula is fully loaded with bone graft. The cannula and the plunger inside the cannula may then be removed from the loading funnel and coupled to an injector assembly for use in surgery.

20 Claims, 19 Drawing Sheets

(56) References Cited

U.S. PATENT DOCUMENTS

| | | | |
|---|---|---|---|
| 5,431,658 A * | 7/1995 | Moskovich | A61B 17/025 606/90 |
| 5,638,997 A | 6/1997 | Hawkins et al. | |
| 5,718,707 A | 2/1998 | Mikhail | |
| 5,785,680 A | 7/1998 | Niezink et al. | |
| 5,827,289 A | 10/1998 | Reiley et al. | |
| 5,893,488 A | 4/1999 | Hoag et al. | |
| 5,925,051 A | 7/1999 | Mikhail | |
| 5,954,728 A | 9/1999 | Heller et al. | |
| 6,010,713 A | 1/2000 | Zhong et al. | |
| 6,048,346 A | 4/2000 | Reiley et al. | |
| 6,086,594 A | 7/2000 | Brown | |
| 6,241,734 B1 | 6/2001 | Scribner et al. | |
| 6,248,110 B1 | 6/2001 | Reiley et al. | |
| 6,383,519 B1 | 5/2002 | Sapieszko et al. | |
| 6,436,143 B1 | 8/2002 | Ross et al. | |
| 6,439,439 B1 | 8/2002 | Rickard et al. | |
| 6,521,246 B2 | 2/2003 | Sapieszko et al. | |
| 6,582,438 B2 | 6/2003 | DeMayo | |
| 6,613,054 B2 | 9/2003 | Scribner et al. | |
| 6,641,587 B2 | 11/2003 | Scribner et al. | |
| 6,645,213 B2 | 11/2003 | Sand et al. | |
| 6,676,664 B1 | 1/2004 | Al-Assir | |
| 6,716,216 B1 | 4/2004 | Boucher et al. | |
| 6,719,761 B1 | 4/2004 | Reiley et al. | |
| 6,726,691 B2 | 4/2004 | Osorio et al. | |
| 6,749,595 B1 | 6/2004 | Murphy | |
| 6,770,079 B2 | 8/2004 | Bhatnagar et al. | |
| 6,783,515 B1 | 8/2004 | Miller et al. | |
| 6,783,534 B2 | 8/2004 | Mehdizadeh | |
| 6,814,736 B2 | 11/2004 | Reiley et al. | |
| 6,899,719 B2 | 5/2005 | Reiley et al. | |
| 6,997,930 B1 | 2/2006 | Jaggi et al. | |
| 7,004,945 B2 | 2/2006 | Boyd et al. | |
| 7,153,306 B2 | 12/2006 | Ralph et al. | |
| 7,153,307 B2 | 12/2006 | Scribner et al. | |
| 7,252,671 B2 | 8/2007 | Scribner et al. | |
| 7,316,689 B2 | 1/2008 | Lieberman | |
| 7,325,995 B2 | 2/2008 | Keller | |
| 7,371,241 B2 | 5/2008 | Evans et al. | |
| 7,524,103 B2 | 4/2009 | McGill et al. | |
| 7,534,451 B2 | 5/2009 | Erbe et al. | |
| 7,575,577 B2 | 8/2009 | Boyd et al. | |
| 7,601,157 B2 | 10/2009 | Boyd et al. | |
| 7,641,664 B2 | 1/2010 | Pagano | |
| 7,704,256 B2 | 4/2010 | Sand et al. | |
| 7,708,742 B2 | 5/2010 | Scribner et al. | |
| 7,731,720 B2 | 6/2010 | Sand et al. | |
| 7,736,049 B2 | 6/2010 | Keller | |
| 7,771,431 B2 | 8/2010 | Scribner et al. | |
| 7,824,359 B2 | 11/2010 | Solomon et al. | |
| 7,828,807 B2 | 11/2010 | LeHuec et al. | |
| 7,883,512 B2 | 2/2011 | Pajunk et al. | |
| 7,887,543 B2 | 2/2011 | Sand et al. | |
| 7,909,833 B2 | 3/2011 | Voellmicke | |
| 7,914,537 B2 | 3/2011 | Boyd et al. | |
| 7,927,339 B2 | 4/2011 | Ralph et al. | |
| 7,938,296 B2 | 5/2011 | Keller | |
| 7,938,835 B2 | 5/2011 | Boucher et al. | |
| 7,955,391 B2 | 6/2011 | Schaller | |
| 7,959,638 B2 | 6/2011 | Osorio et al. | |
| 7,967,827 B2 | 6/2011 | Osorio et al. | |
| 7,972,340 B2 | 7/2011 | Sand et al. | |
| 8,016,808 B2 | 9/2011 | Keller | |
| 8,038,651 B2 | 10/2011 | Keller | |
| 8,074,843 B2 | 12/2011 | Keller | |
| 8,096,449 B2 | 1/2012 | Keller | |
| 8,100,295 B2 | 1/2012 | Keller | |
| 8,123,756 B2 | 2/2012 | Miller et al. | |
| 8,162,967 B1 | 4/2012 | Kaiser et al. | |
| 8,167,835 B2 | 5/2012 | Keller | |
| 8,226,717 B2 | 7/2012 | Osorio et al. | |
| 8,240,511 B2 | 8/2012 | Greter et al. | |
| 8,246,627 B2 | 8/2012 | Vanleeuwen et al. | |
| 8,246,681 B2 | 8/2012 | Osorio et al. | |
| 8,256,646 B2 | 9/2012 | Keller | |
| 8,282,648 B2 | 10/2012 | Tekulve | |
| 8,317,865 B2 | 11/2012 | Osorio et al. | |
| 8,328,052 B2 | 12/2012 | Hung | |
| 8,348,955 B2 | 1/2013 | Truckai et al. | |
| 8,409,211 B2 | 4/2013 | Baroud | |
| 8,419,730 B2 | 4/2013 | Pellegrino et al. | |
| 8,439,929 B1 | 5/2013 | Sharratt et al. | |
| 8,439,930 B2 | 5/2013 | Campion et al. | |
| 8,444,025 B2 | 5/2013 | Greter et al. | |
| 8,454,620 B2 | 6/2013 | Ralph et al. | |
| 8,454,663 B2 | 6/2013 | Boucher et al. | |
| 8,460,235 B2 | 6/2013 | Keller | |
| 8,486,067 B2 | 7/2013 | Anthony et al. | |
| 8,491,592 B2 | 7/2013 | Dubach | |
| 8,505,545 B2 | 8/2013 | Conquergood et al. | |
| 8,506,572 B2 | 8/2013 | Evans et al. | |
| 8,517,226 B2 | 8/2013 | Keller | |
| 8,524,798 B2 | 9/2013 | Seaton, Jr. et al. | |
| 8,534,575 B2 | 9/2013 | Brem | |
| 8,562,619 B2 | 10/2013 | Liao et al. | |
| 8,562,620 B2 | 10/2013 | Truckai et al. | |
| 8,590,747 B2 | 11/2013 | Keller | |
| 8,603,096 B2 | 12/2013 | Agard et al. | |
| 8,603,097 B2 | 12/2013 | Shah et al. | |
| 8,608,750 B2 | 12/2013 | Faccioli et al. | |
| 8,622,244 B2 | 1/2014 | Stoeckli et al. | |
| 8,628,536 B2 | 1/2014 | Walker et al. | |
| 8,672,193 B2 | 3/2014 | Vukic et al. | |
| 8,685,031 B2 | 4/2014 | Kleiner et al. | |
| 8,690,012 B2 | 4/2014 | Stoeckli et al. | |
| 8,696,678 B2 | 4/2014 | Foster | |
| 8,702,741 B2 | 4/2014 | Jaggi et al. | |
| 8,709,088 B2 | 4/2014 | Kleiner et al. | |
| 8,721,600 B2 | 5/2014 | Henniges et al. | |
| 8,733,593 B2 | 5/2014 | Brem et al. | |
| 8,777,479 B2 | 7/2014 | Kwan et al. | |
| 8,777,956 B2 | 7/2014 | Hoeppner et al. | |
| 8,795,702 B2 | 8/2014 | Greenspan et al. | |
| 8,801,723 B2 | 8/2014 | Shah et al. | |
| 8,814,942 B2 | 8/2014 | Anthony et al. | |
| 8,827,981 B2 | 9/2014 | Liu et al. | |
| 8,840,593 B2 | 9/2014 | Greter et al. | |
| 8,845,647 B2 | 9/2014 | Grebius | |
| 8,852,200 B2 | 10/2014 | Steffen et al. | |
| 8,876,834 B2 | 11/2014 | Bonnin et al. | |
| 8,905,996 B2 | 12/2014 | Vandewalle | |
| 8,906,028 B2 | 12/2014 | Kleiner et al. | |
| 8,915,413 B2 | 12/2014 | Kayser | |
| 8,932,297 B2 | 1/2015 | O'Halloran et al. | |
| 8,936,391 B2 | 1/2015 | Stoeckli et al. | |
| 8,939,985 B2 | 1/2015 | Agard et al. | |
| 8,944,107 B2 | 2/2015 | Greter et al. | |
| D723,682 S | 3/2015 | Kleiner et al. | |
| 8,992,541 B2 | 3/2015 | Ferreyro et al. | |
| 9,060,877 B2 | 6/2015 | Kleiner | |
| 9,144,629 B2 | 9/2015 | Pomrink et al. | |
| 9,173,694 B2 | 11/2015 | Kleiner | |
| 9,186,193 B2 | 11/2015 | Kleiner et al. | |
| 9,198,936 B2 | 12/2015 | Greenspan et al. | |
| 9,199,006 B2 | 12/2015 | Pomrink et al. | |
| 9,199,032 B2 | 12/2015 | McBride et al. | |
| D750,249 S | 2/2016 | Grimberg, Jr. et al. | |
| 2002/0049449 A1 | 4/2002 | Bhatnagar et al. | |
| 2004/0044412 A1 * | 3/2004 | Lambrecht | A61F 2/4611 623/17.16 |
| 2004/0215201 A1 * | 10/2004 | Lieberman | A61F 2/4601 606/93 |
| 2005/0004578 A1 * | 1/2005 | Lambrecht | A61B 17/70 606/102 |
| 2005/0105384 A1 | 5/2005 | Eder et al. | |
| 2005/0113762 A1 | 5/2005 | Kay et al. | |
| 2005/0288795 A1 | 12/2005 | Bagga et al. | |
| 2007/0055282 A1 | 3/2007 | Muschler | |
| 2007/0185496 A1 | 8/2007 | Beckman et al. | |
| 2007/0213655 A1 | 9/2007 | Prusmack | |
| 2008/0056065 A1 | 3/2008 | Keller | |
| 2008/0065083 A1 * | 3/2008 | Truckai | A61B 17/3472 600/407 |

(56) References Cited

U.S. PATENT DOCUMENTS

| | | |
|---|---|---|
| 2008/0065091 A1 | 3/2008 | Scribner et al. |
| 2008/0073372 A1 | 3/2008 | Keller |
| 2008/0249530 A1 | 10/2008 | Truckai et al. |
| 2009/0024104 A1 | 1/2009 | Keller |
| 2009/0127288 A1 | 5/2009 | Keller |
| 2009/0127289 A1 | 5/2009 | Keller |
| 2009/0134186 A1 | 5/2009 | Keller |
| 2009/0192460 A1 | 7/2009 | Keller |
| 2009/0230214 A1 | 9/2009 | Keller |
| 2009/0255960 A1 | 10/2009 | Keller |
| 2009/0302060 A1 | 12/2009 | Keller |
| 2009/0314803 A1 | 12/2009 | Keller |
| 2009/0318925 A1 | 12/2009 | Campion et al. |
| 2010/0163579 A1 | 7/2010 | Keller |
| 2010/0198140 A1 | 8/2010 | Lawson |
| 2010/0256648 A1 | 10/2010 | Kuslich et al. |
| 2010/0262152 A1 | 10/2010 | Shadduck et al. |
| 2010/0268232 A1 | 10/2010 | Betz et al. |
| 2010/0282774 A1 | 11/2010 | Greter et al. |
| 2010/0288790 A1 | 11/2010 | Keller |
| 2011/0004156 A1 | 1/2011 | Keller |
| 2011/0021982 A1 | 1/2011 | Keller |
| 2011/0108573 A1 | 5/2011 | Stoeckli et al. |
| 2011/0114212 A1 | 5/2011 | Greter et al. |
| 2011/0118664 A1 | 5/2011 | Greter et al. |
| 2011/0121035 A1 | 5/2011 | Greter et al. |
| 2011/0138741 A1 | 6/2011 | Stoeckli et al. |
| 2011/0139821 A1 | 6/2011 | Greter et al. |
| 2011/0228631 A1 | 9/2011 | Stoeckli et al. |
| 2011/0238184 A1 | 9/2011 | Zdeblick et al. |
| 2011/0253806 A1 | 10/2011 | Brem |
| 2011/0264098 A1 | 10/2011 | Cobbs |
| 2011/0264099 A1 | 10/2011 | Quinto |
| 2011/0278375 A1 | 11/2011 | Greter et al. |
| 2011/0295212 A1 | 12/2011 | Greter et al. |
| 2012/0026823 A1 | 2/2012 | Greter et al. |
| 2012/0039147 A1 | 2/2012 | Greter et al. |
| 2012/0053642 A1 | 3/2012 | Lozier et al. |
| 2012/0055580 A1 | 3/2012 | Greter |
| 2012/0065613 A1 | 3/2012 | Pepper et al. |
| 2012/0078352 A1 | 3/2012 | Wang et al. |
| 2012/0111897 A1 | 5/2012 | Vukic et al. |
| 2012/0175384 A1 | 7/2012 | Greter et al. |
| 2012/0199607 A1 | 8/2012 | Keller |
| 2012/0298254 A1 | 11/2012 | Brem et al. |
| 2012/0302986 A1 | 11/2012 | Brem et al. |
| 2012/0316509 A1 | 12/2012 | Kayser et al. |
| 2012/0325367 A1 | 12/2012 | Mathys et al. |
| 2012/0330229 A1 | 12/2012 | Greter |
| 2012/0330320 A1 | 12/2012 | Takizawa et al. |
| 2013/0023833 A1 | 1/2013 | Kayser |
| 2013/0023885 A1 | 1/2013 | Madden et al. |
| 2013/0023887 A1 | 1/2013 | Bogert et al. |
| 2013/0032623 A1 | 2/2013 | Kayser |
| 2013/0048670 A1 | 2/2013 | Greter |
| 2013/0087578 A1 | 4/2013 | Brem et al. |
| 2013/0098942 A1 | 4/2013 | Greter |
| 2013/0131683 A1 | 5/2013 | Shah et al. |
| 2013/0144249 A1 | 6/2013 | Fenton et al. |
| 2013/0190680 A1 | 7/2013 | Baroud |
| 2013/0206137 A1 | 8/2013 | Greter |
| 2013/0226188 A1 | 8/2013 | Campion et al. |
| 2013/0296828 A1 | 11/2013 | Schon et al. |
| 2013/0330410 A1 | 12/2013 | Pomrink et al. |
| 2013/0331846 A1 | 12/2013 | Smith et al. |
| 2013/0331847 A1 | 12/2013 | Smith et al. |
| 2014/0058399 A1 | 2/2014 | Shah et al. |
| 2014/0079789 A1 | 3/2014 | Pomrink et al. |
| 2014/0098629 A1 | 4/2014 | Greter |
| 2014/0163519 A1 | 6/2014 | Shadduck et al. |
| 2014/0213999 A1 | 7/2014 | Geisert |
| 2014/0221967 A1 | 8/2014 | Childs et al. |
| 2014/0251141 A1 | 9/2014 | Hoogenakker et al. |
| 2014/0252044 A1 | 9/2014 | Greter et al. |
| 2014/0257232 A1 | 9/2014 | Mathur et al. |
| 2014/0261082 A1 | 9/2014 | Anderson et al. |
| 2014/0271912 A1 | 9/2014 | Pomrink et al. |
| 2014/0271913 A1 | 9/2014 | Pomrink et al. |
| 2014/0324013 A1 | 10/2014 | Shadeck et al. |
| 2014/0350520 A1 | 11/2014 | Drontle et al. |
| 2014/0371740 A1 | 12/2014 | Germain et al. |
| 2015/0030684 A1 | 1/2015 | Pomrink et al. |
| 2015/0079146 A1 | 3/2015 | Pomrink et al. |
| 2015/0112352 A1 | 4/2015 | Krause et al. |
| 2015/0238654 A1 | 8/2015 | Pomrink et al. |

FOREIGN PATENT DOCUMENTS

| | | |
|---|---|---|
| WO | 0009024 A1 | 2/2000 |
| WO | 03000121 A2 | 1/2003 |
| WO | 2004002375 A1 | 1/2004 |
| WO | 2004100771 A2 | 11/2004 |
| WO | 2005060367 A2 | 7/2005 |
| WO | 2006002430 A2 | 1/2006 |
| WO | 2007022194 A2 | 2/2007 |
| WO | 2007028253 A2 | 3/2007 |
| WO | 2007122006 A1 | 11/2007 |
| WO | 2009158317 A1 | 12/2009 |
| WO | 2010044462 A1 | 4/2010 |
| WO | 2010127462 A1 | 11/2010 |
| WO | 2011109581 A1 | 9/2011 |
| WO | 2011111653 A1 | 9/2011 |
| WO | 2012043247 A1 | 4/2012 |
| WO | 2012151253 A1 | 11/2012 |
| WO | 2013025504 A1 | 2/2013 |
| WO | 2014055734 A2 | 4/2014 |
| WO | 2014099967 A1 | 6/2014 |

OTHER PUBLICATIONS

European Search Report for Application No. EP14189839 dated Jan. 26, 2015.

Extended European Search Report for Application No. EP16165836 dated Jun. 16, 2016.

Extended European Search Report for Application No. EP17185236.1 dated Jan. 19, 2018.

* cited by examiner

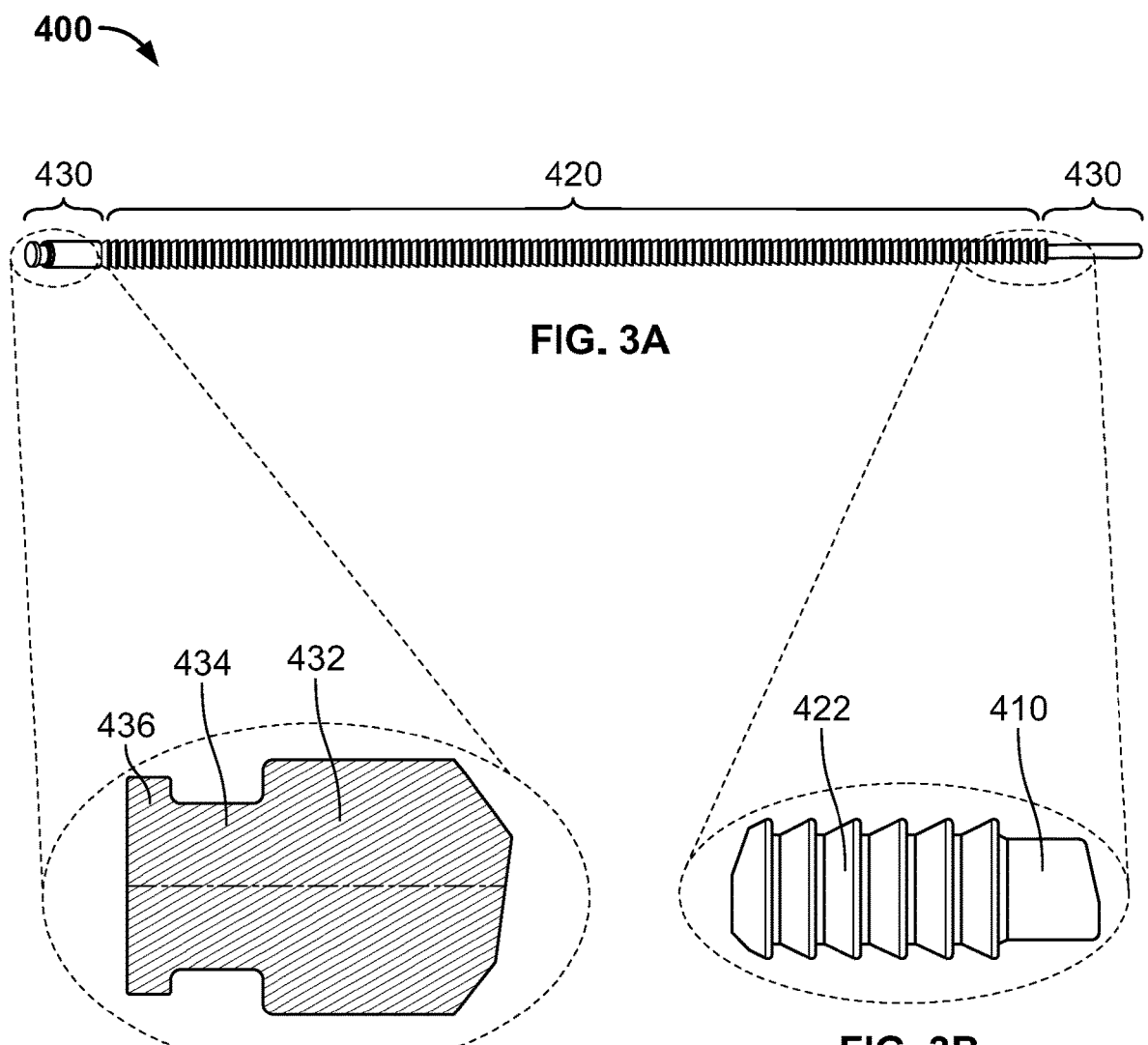

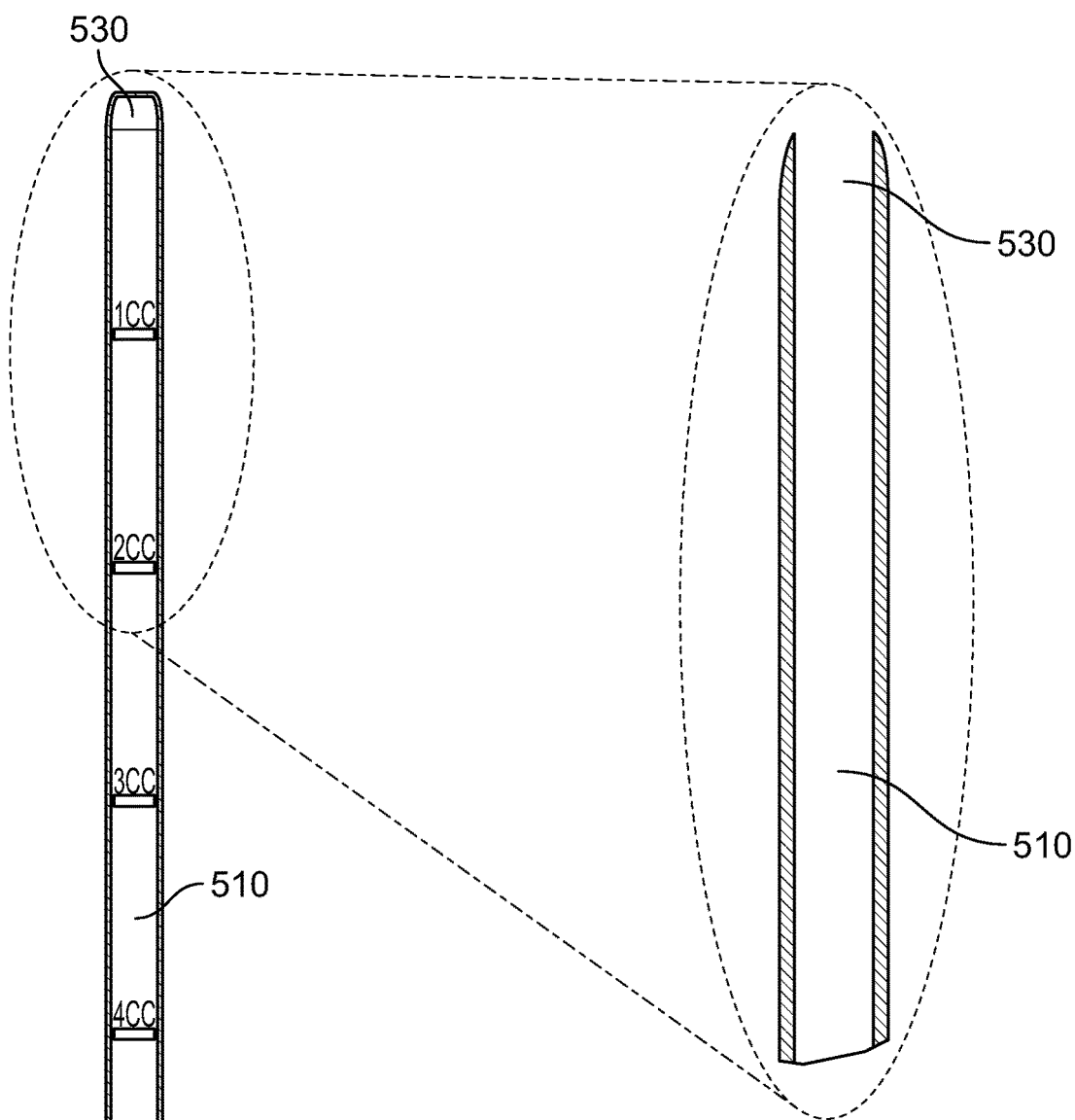
FIG. 4D
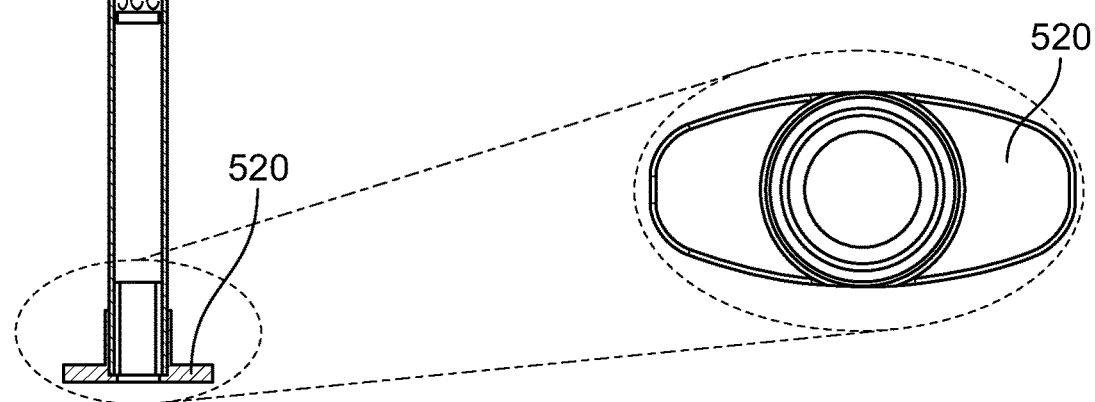
FIG. 4C
FIG. 4B

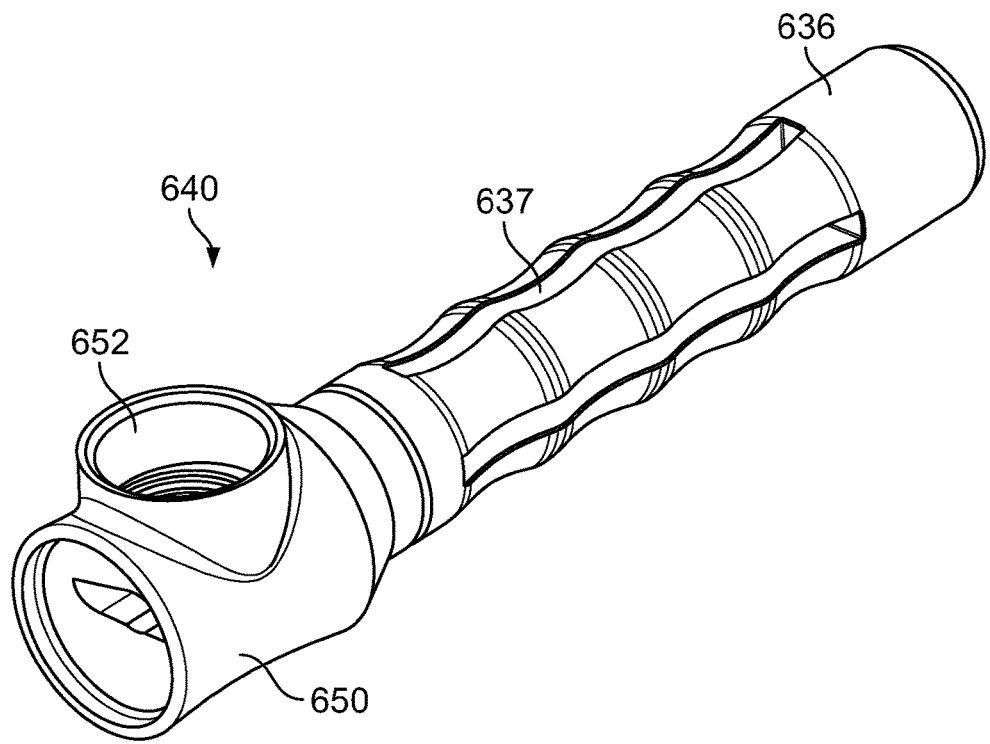
FIG. 5D
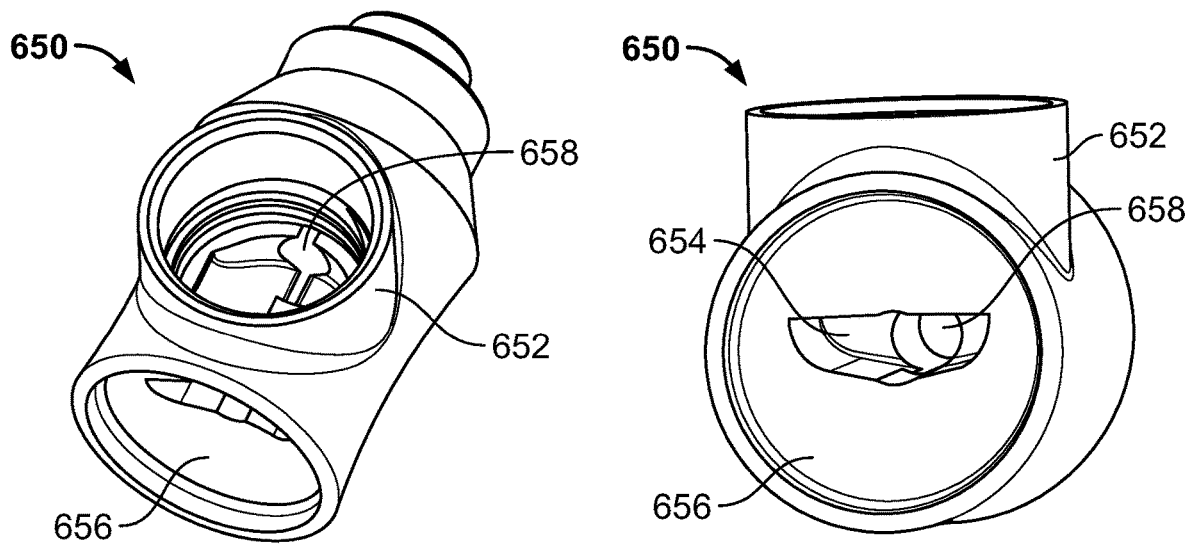
FIG. 5E
FIG. 5F

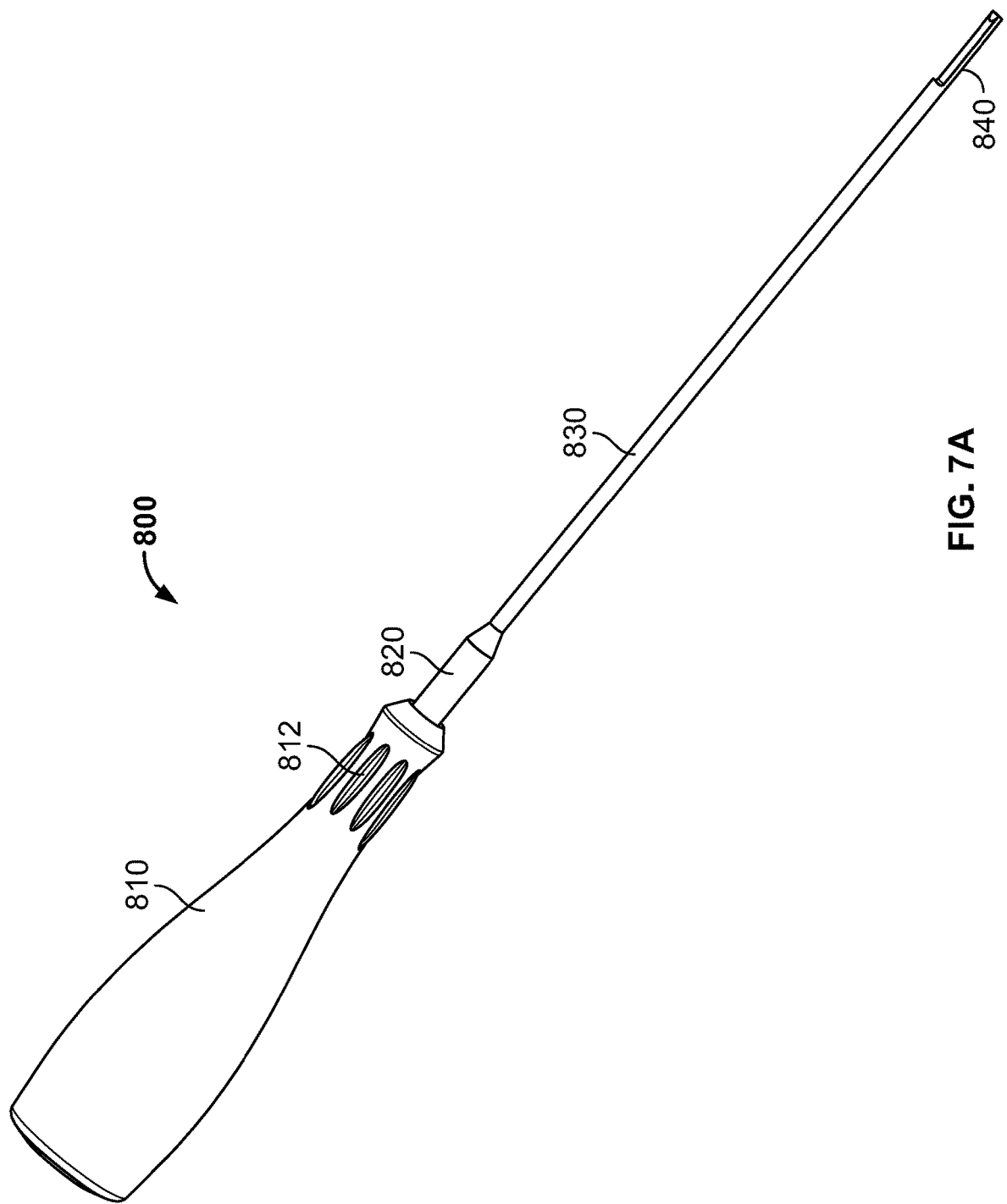

BONE GRAFT DELIVERY LOADING ASSEMBLY

CROSS-REFERENCE TO RELATED APPLICATIONS

This application is a continuation of U.S. patent application Ser. No. 15/241,339, filed on Aug. 19, 2016, the disclosure of which is hereby incorporated by reference herein.

FIELD OF THE DISCLOSURE

The present disclosure relates to systems for delivering materials to bone during a surgical procedure, and more particularly methods and systems for loading the materials into the delivery systems.

BACKGROUND

There is an increasing prevalence in minimally invasive spinal procedures. For instance, percutaneous delivery of bone graft or bone graft substitute to aid implants or screws (also potentially delivered percutaneously) in fixing and/or fusing portions of the spinal column. However, there are challenges to delivering such bone graft materials percutaneously during minimally invasive surgical procedures. As used herein, the term "bone graft" includes, but is not limited to bone graft, bone graft alternative, bone graft substitute, bone marrow aspirate, demineralized bone matrix, or mixtures thereof, whether occurring naturally or artificially, unless specified otherwise. It should further be understood that the term bone graft may refer to, separately or in combination with any or all of the materials provided above, bone marrow aspirate, blood, and saline.

Currently, in certain surgical procedures, bone graft is provided to a surgeon in a pre-loaded syringe. The surgeon may transfer the bone graft from the syringe to an injector device with the syringe and the injector device being aligned along the same axis. However, using pre-loaded bone graft may reduce the ability of the surgeon to use a particular desired bone graft for a particular procedure. Further, loading bone graft from a syringe to an injector device with both components aligned along the same axis may be difficult because bone graft materials may behave as non-Newtonian fluids. For example, some bone graft materials do not flow easily, particularly through funnel-like or conical geometries, from a relatively large holding area, such as a cylinder or tube, to a relatively small holding area.

Therefore, there exists a need for an improved bone graft delivery loading assembly and methodology that addresses these and other drawbacks with prior art systems.

BRIEF SUMMARY

According to one embodiment of the disclosure, a bone graft loading system includes a loading member having a passageway extending along a first longitudinal axis, a container adapted to contain the bone graft, the container extending along a second longitudinal axis, and a cannula member having an inner hollow space extending along a third longitudinal axis. When the cannula member is received within the passageway of the loading member and the container is coupled to the loading member, the first and third longitudinal axes are parallel to one another and transverse to the third longitudinal axis. The container may be a syringe member adapted to couple to a syringe docking portion of the loading member. A locking member may be positioned on a first end of the loading member, the locking member having two extension members and being rotatable about the first longitudinal axis. A proximal end of the cannula member may include a flange. When the cannula member is received within the passageway of the loading member, the locking member may be capable of rotation between a locked state in which the extension members of the locking member inhibit proximal movement of the flange of the cannula member with respect to the loading member and an unlocked state in which the flange of the cannula member is capable of proximal movement with respect to the loading member.

A flange may extend radially outward from the loading member, and a spring may be positioned between the flange of the loading member and the locking member, the spring biasing the locking member toward the first end of the loading member. The syringe docking portion may include a cylindrical member extending orthogonally from the longitudinal axis of the loading member, the syringe docking portion including a first mating feature and the syringe member including a second mating feature adapted to couple to the first mating feature. The first mating feature may include threads on an interior surface of the cylindrical member of the syringe docking portion, and the second mating feature may include threads on an exterior surface of a distal end of the syringe member.

A plunger member may be adapted to be received within the inner hollow space of the cannula member. The plunger member may include a plurality of teeth along a length of the plunger member. An elastomeric seal may be adapted to couple to a distal tip of the plunger member. When the plunger member is received within the inner hollow space of the cannula member, the elastomeric seal may form a fluid tight seal between the elastomeric seal and the inner hollow space of the cannula member.

The syringe docking portion may include a first face with an opening therein, and an aperture in fluid communication with the passageway of the loading member. When the cannula member is received within the passageway of the loading member, an open distal tip of the cannula member may be positioned adjacent the aperture of the syringe docking portion. The aperture of the syringe docking portion may have a diameter that is smaller than a diameter of the open distal tip of the cannula member. The first face may have a concave profile. When the syringe member is coupled to the syringe docking portion, a distal end of the syringe member may be positioned between the opening in the first face of the syringe docking portion and the aperture of the syringe docking portion. A loading tool may have a handle and a cylindrical shaft extending distally from the handle. The cylindrical shaft may have an external diameter that is smaller than a diameter of the aperture of the syringe docking portion and also smaller than a diameter of the inner hollow space of the cannula. The loading tool may include a distal tip portion extending distally from the cylindrical shaft, the distal tip portion having the shape of a half cylinder. A terminal end of the distal tip portion of the loading tool may include a recess having a shape of a portion of a sphere.

According to another aspect of the disclosure, a method of loading bone graft into a bone graft delivery system includes (i) coupling a syringe member containing bone graft to a loading member so that a longitudinal axis of the syringe member is transverse to a longitudinal axis of the loading member; (ii) positioning a cannula member within a passageway of the loading member so that a longitudinal axis of the cannula member is parallel to the longitudinal axis of the loading member; (iii) advancing bone graft from the syringe to the loading member; and (iv) inserting a loading tool into an interior space of the cannula to advance bone graft from the holding area to the interior space of the cannula. The method may include repeating steps (iii) and (iv). A plunger member may be inserted into the interior space of the cannula member prior to positioning the cannula member within the passageway of the loading member. An elastomeric seal may be positioned onto a distal tip of the plunger member prior to inserting the plunger member into the interior space of the cannula. Prior to positioning the elastomeric seal onto the distal tip of the plunger, the elastomeric seal may be positioned within a sterile package. The sterile package may include a base portion connected to a lid portion by a hinge, and the hinge may bias the lid portion away from the base portion into an open condition in the absence of applied force. The step of inserting the plunger member into the interior space of the cannula member may include forming a fluid tight seal between the elastomeric seal and the interior space of the cannula member.

The method may further include removing the cannula member from the loading member while the plunger member is still within the cannula member, and then coupling the cannula member and the plunger member to a handle assembly adapted to advance the plunger member relative to the cannula member. The step of positioning the cannula member within the passageway of the loading member may include advancing the cannula member until a proximal flange of the cannula member contacts the loading member. A locking hub of the loading member may be rotated so that extension members of the locking hub overlie the proximal flange of the cannula member. The bone graft may be manually loaded into the syringe member prior to coupling the syringe member to the loading member. The step of coupling the syringe member to the loading member may be performed so that the longitudinal axis of the syringe member is orthogonal to the longitudinal axis of the loading member. The bone graft advanced from the syringe to the loading member may be first advanced to a holding area of the loading member that is spaced apart from the cannula member. The step of inserting the loading tool into the interior space of the cannula may include inserting the loading tool through the holding area.

BRIEF DESCRIPTION OF THE DRAWINGS

FIGS. 3A-C are various views of a plunger subassembly of the injector assembly of FIG. 1.

FIGS. 4A-D are various views of a delivery tube subassembly of the injector assembly of FIG. 1.

FIGS. 5A-F are various views of a loading funnel according to an embodiment of the disclosure.

FIGS. 7A-C are various views of a loading tool according to an embodiment of the disclosure.

DETAILED DESCRIPTION

As used herein, the term "proximal" refers to a location closer to a surgeon or other personnel using the device as described herein, while the term "distal" refers to a location farther away from the surgeon using the device.

Figure 1:
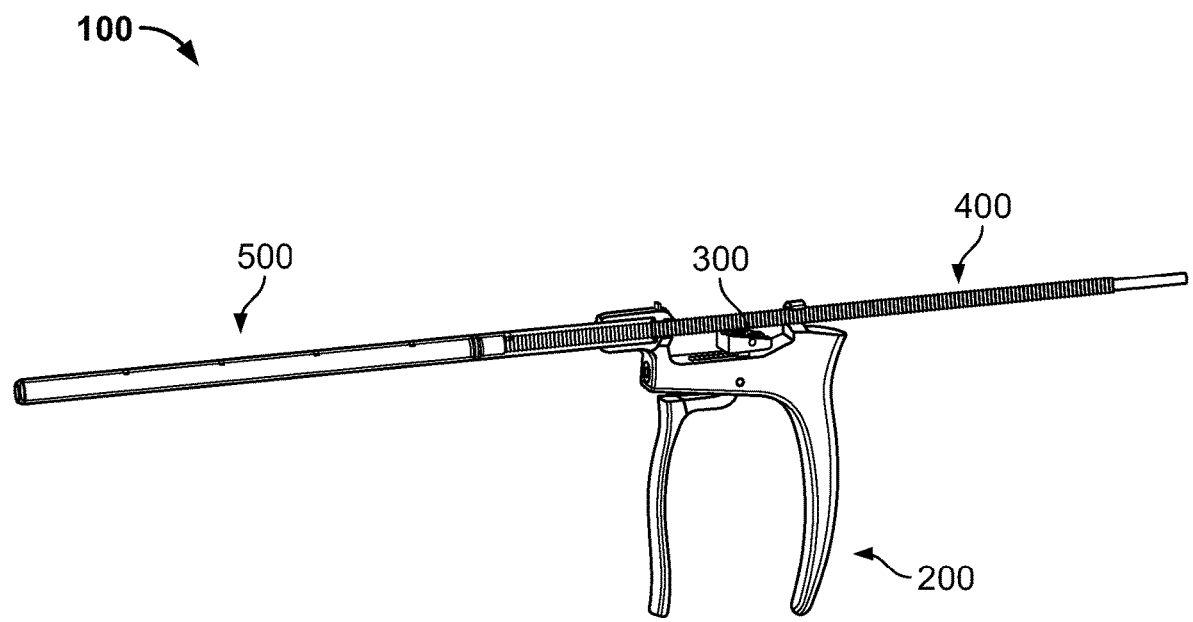
FIG. 1 is a perspective view of a bone graft injector assembly according to an embodiment of the disclosure.

An injector assembly 100 of a bone graft delivery system is illustrated in FIG. 1 according to an embodiment of the disclosure. Injector assembly includes a number of subassemblies including, for example, a handle subassembly 200, a ratchet subassembly 300, a plunger subassembly 400, and a delivery tube subassembly 500. Handle subassembly 200 may be used to advance plunger subassembly 400 in an incremental or continuous fashion through delivery tube subassembly 500 to force a material out of a distal end thereof. For embodiments with incremental advancement of plunger subassembly 400, handle subassembly 200 and the plunger subassembly may work in conjunction with ratchet subassembly 300 to facilitate the incremental advancement.

Figure 2A:
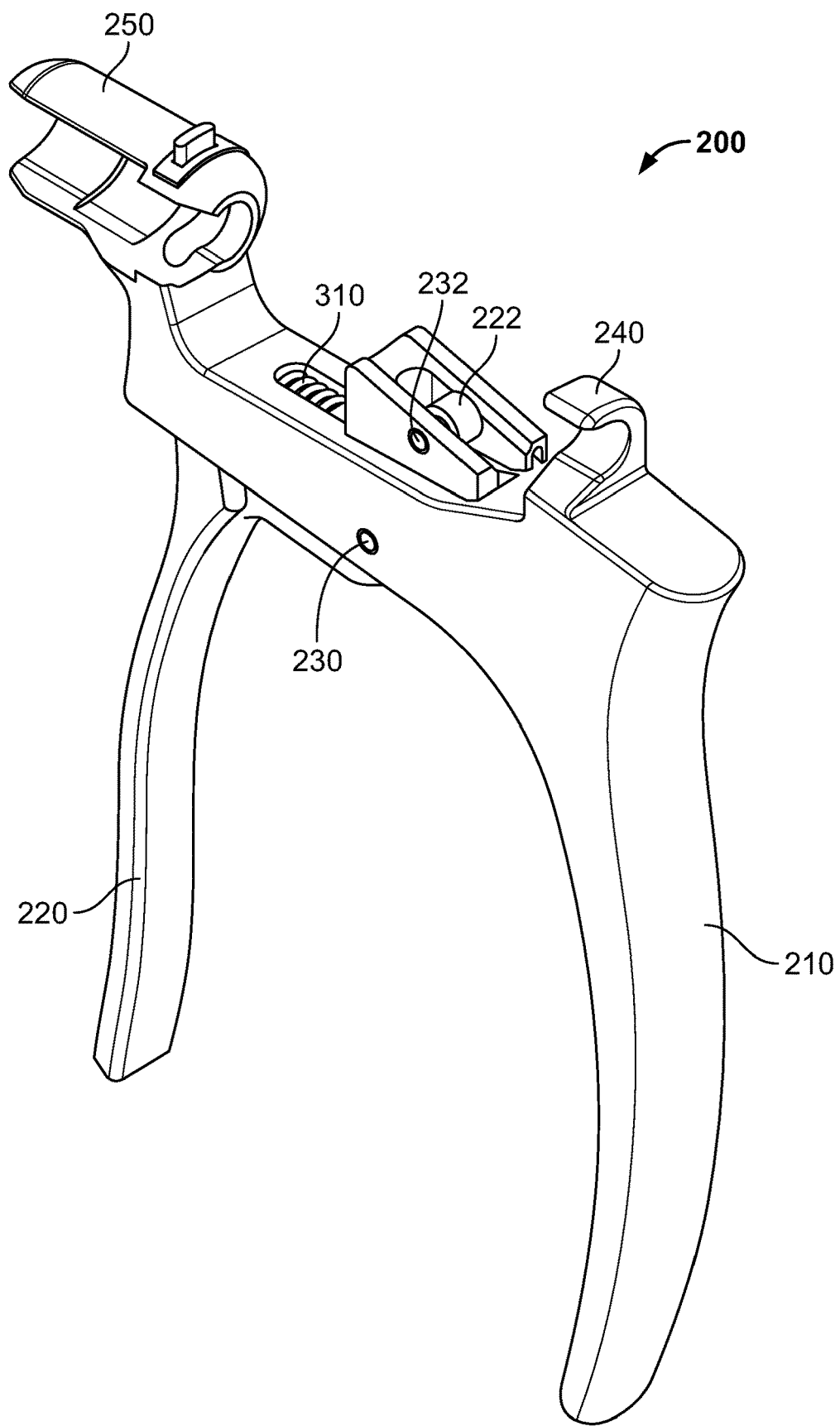
FIGS. 2A-C are various views of a handle subassembly of the injector assembly of FIG. 1.
Figure 2B:
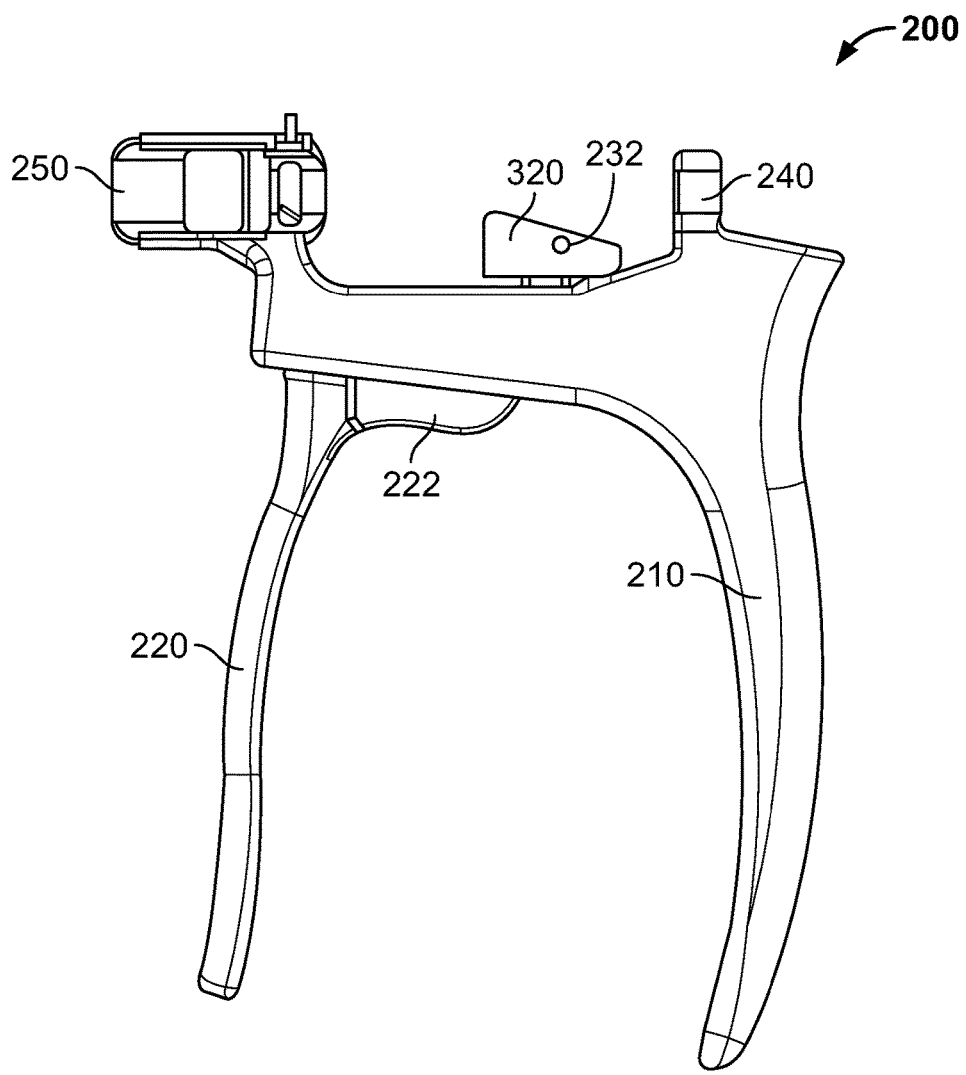
Figure 2C:
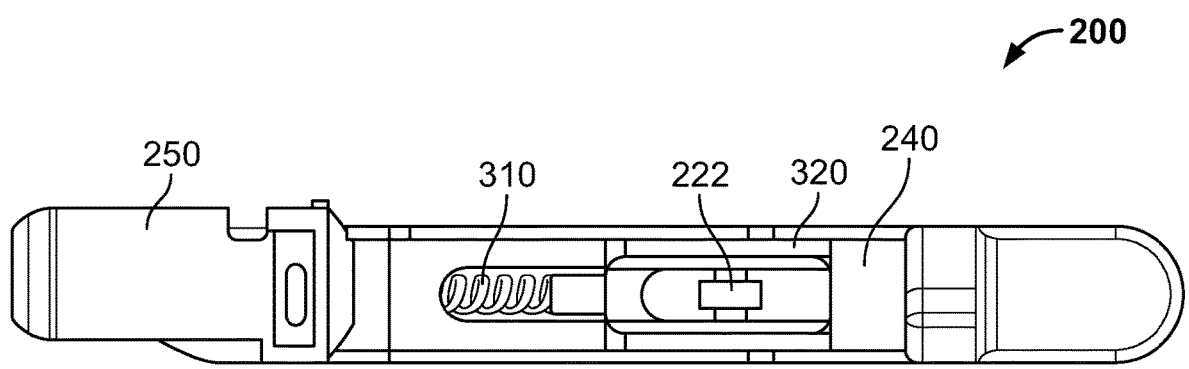

Handle subassembly 200, illustrated in FIGS. 2A-C, includes a fixed arm 210 coupled to a moving arm 220 by a fastener, for example a pivot pin 230. A first retaining feature 240 may extend from a superior proximal portion of fixed arm 210. First retaining feature 240 may be generally "U" or "C" shaped, forming a laterally facing recess sized and shaped to receive a portion of plunger subassembly 400. A second retaining feature 250 extends from a superior distal portion of fixed arm 210. Second retaining feature 250 may also be generally "U" or "C" shaped, forming a laterally facing recess sized and shaped to receive a portion of delivery tube subassembly 500. For instance, second retaining feature 250 may include a slot 252 to receive a flange 520 of cannula 510 securely therein, which is described in greater detail below.

Moving arm 220 includes an upwardly extending member 222 configured to extend through a slot in fixed arm 210. Upwardly extending member 222 may include a first aperture to receive pivot pin 230 so that moving arm 220 may pivot with respect to fixed arm 210. Upwardly extending member 222 may include a second aperture at a superior end to receive another fastener such as pin 232 for coupling to a portion of ratchet subassembly 300.

Ratchet subassembly 300 includes a spring 310 and a pawl 320. Spring 310 may be positioned within the slot of fixed arm 210, with a first end of the spring 310 abutting a distal end of the slot and a second end of the spring 310 abutting a portion of upwardly extending member 222 of moving arm 220. With this configuration, fixed handle 210 is biased away from moving handle 220 about pivot pin 230 by spring 310. In other words, a user may squeeze moving arm 220 toward fixed arm 210, which advances pawl 320 distally while compressing spring 310. As the user relaxes the grip, moving arm 220 will move distally with respect to fixed arm 210 as spring 310 decompresses and pawl 320 moves proximally. Pawl 310 may have a substantially flat distal face so that, as a user squeezes fixed arm 210 and moving arm 220 causing pawl 310 to advance forward, the flat distal face and/or a corner thereof engages a surface of a component of plunger subassembly 400, which is described in greater detail below, causing plunger subassembly 400 to advance forward with each iterative squeeze. Upon releasing compression of the moving arm 220, the pawl 310 may pivot slightly about pin 232, allowing for pawl 310 to easily move proximally without engaging any other surfaces of plunger subassembly 400, ensuring that one cycle of squeezing and releasing moving arm 220 only advances plunger subassembly 400 distally. All portions of handle subassembly 200 and ratchet subassembly 300 may be formed of materials suitable for use in surgery, including metals. Preferably, the materials are capable of being sterilized such that handle subassembly 200 and ratchet subassembly 300 may be reused. Other injector assemblies that may be suitable for use according to the present disclosure are described in greater detail in U.S. Patent Publication No. 2015/0112352 ("the '352 Publication), the contents of which are hereby incorporated by reference herein.

Figure 3D:
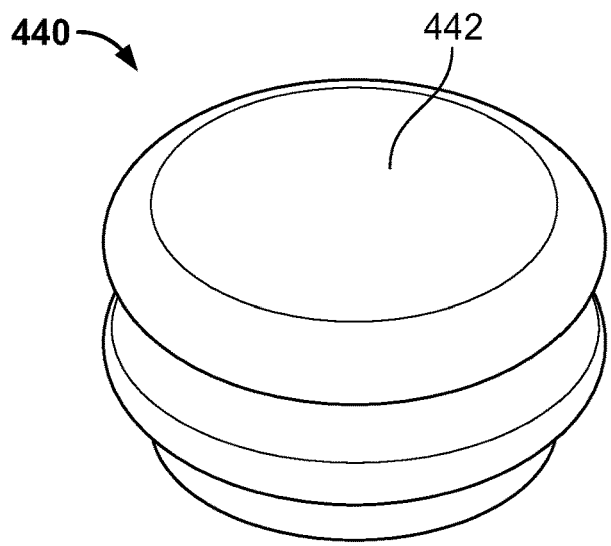
FIGS. 3D-F are various views of a seal member of the plunger subassembly of FIGS. 3A-C.

Plunger subassembly 400 is illustrated in FIGS. 3A-F. Generally, plunger subassembly 400 includes a proximal shaft 410, a main shaft 420, and a distal tip portion 430. Each of proximal shaft 410, main shaft 420, and distal tip portion 430 may be generally cylindrically, with or without additional features. Proximal tip 410 may be cylindrical without any additional features. Main shaft 420 may also be cylindrical, but include a plurality of teeth 422 positioned along the length of the main shaft 420, as best seen in FIG. 3B. Each tooth 422 may have a substantially trapezoidal shape in cross section, such that the distal end of each tooth 422 has a diameter that is smaller than the diameter of the proximal end of each tooth 422. The proximal end of each tooth 422 may have a sharp transition into the distal end of the adjacent tooth 422 so that the distal face of pawl 310 can easily and securely engage the proximal face of a tooth 422. All of the teeth 422 may be substantially identical in shape and size as all other teeth 422. The distal tip portion 430 is best illustrated in FIG. 3C. Distal tip portion 430 may include a cylindrical portion 432 having a diameter approximately equal to the diameter of the largest portion of teeth 422, with a transition into a recessed portion 434. A flange 436 may be positioned distal to the recessed portion 434. Preferably, plunger subassembly 400 is formed of a metal suitable for surgical use so that plunger subassembly 400 may be sterilized and reused, with the exception of seal member 440.

Figure 3E:
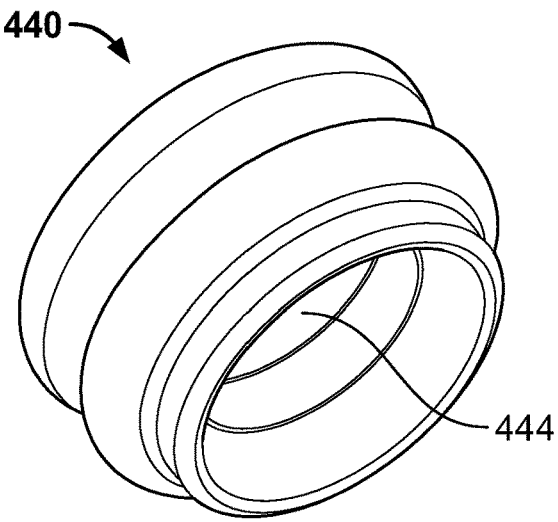
Figure 3F:
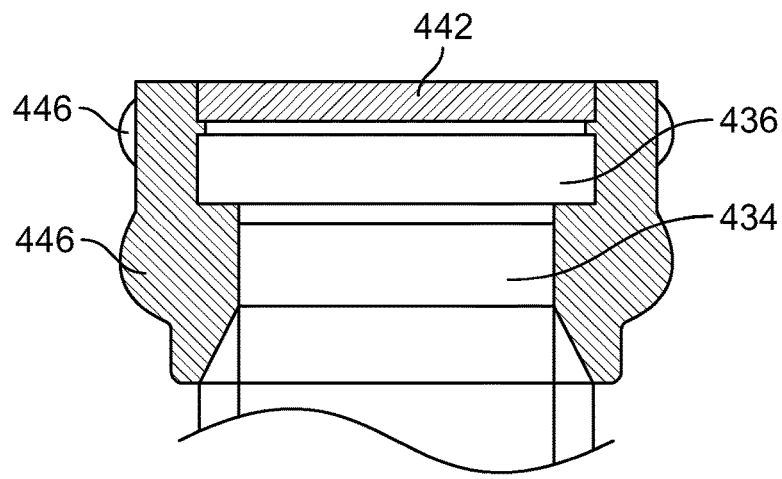

Seal member 440 is best illustrated in FIGS. 3D-E. Seal member 440 may be formed of a rubber or plastic material suitable for a single use, as opposed to the other portions of plunger subassembly 400 that may be reusable. Seal member 440 may include a substantially flat distal face 442 intended for contacting bone graft material as the plunger subassembly 400 advances due to actuation of handle subassembly 200. Seal member 440 may be substantially hollow with an opening 444 on a proximal end thereof. The hollow recess of seal member 440 may have a shape corresponding to the flange 436 and recessed portion 434 of distal tip portion 430 so that the seal member 440 may be snugly secured on the distal tip portion 430 during use, and then removed and disposed after use. The connection between seal member 440 and distal tip portion 430 is best seen in FIG. 3F. Seal member 440 may also include one or more annular ridges 446. When seal member 440 is coupled to the distal tip portion 430, the ridges 446 have a diameter greater than any other portion of plunger subassembly 400. With this configuration, when plunger subassembly 400 is inserted within the delivery tube subassembly 500, the ridges 446 of seal member 440 may have a tight fit within the delivery tube subassembly 500.

Figure 3G:
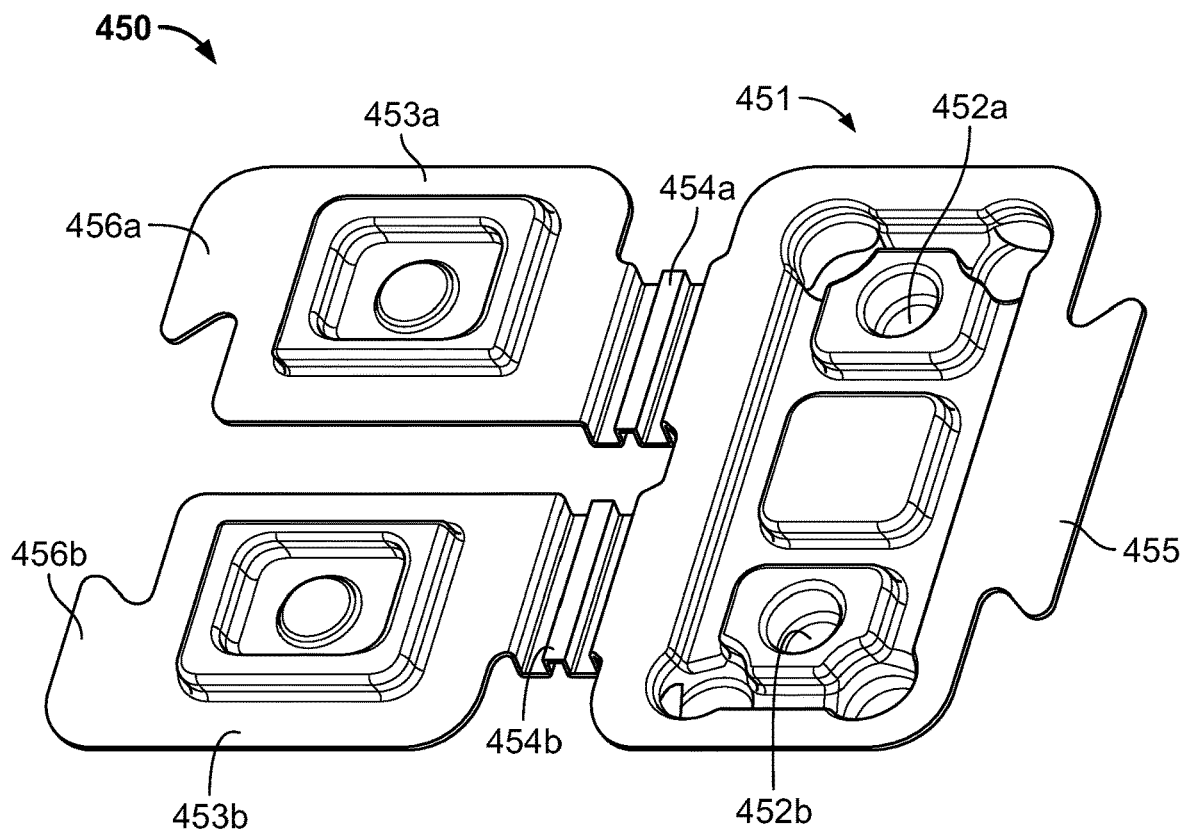
FIG. 3G is a perspective view of packaging to store the seal member of FIGS. 3D-F or other components.

FIG. 3G shows an example of packaging 450 that may be used to store one or more seal members 440 prior to connection to plunger subassembly 400. Packaging 450 may be formed as a single integral piece or multiple pieces, and may be formed from any suitable material such as sturdy plastic material that is preferably translucent. Packaging 450 includes a base member 451 with two recesses 452a, 452b that both correspond to the geometry of a seal member 440, so that a seal member 440 may be securely positioned within each recess 452a, 452b with opening 444 of each seal member 440 facing away from the packaging. Packaging 450 may include first and second lid portions 453a, 453b corresponding to recesses 452a, 452b. Each lid portion 453a, 453b may be coupled to the base member 451 by corresponding hinge members 454a, 454b. Hinge members 454a, 454b are shown as living hinges, although other types of hinges may be suitable. Preferably, hinge members 454a, 454b are biased so that, in the absence of applied forces, lid portions 453a, 453b remain in the open condition shown in FIG. 3G with respect to the base portion 451. The base portion 451 may include a base tab 455, and each lid 453a, 453b may include a corresponding lid tab 456a, 456b. Lid tabs 456a, 456b may each include extensions that fold under, or interlock with, corresponding extensions of base tab 455. With the above-described configuration, a user may simply release the connection between lid tab 456a and base tab 455 to cause lid portion 453a to spring open, or release the connection between lid tab 456b and base tab 455 to cause lid portion 453b to spring open. Once either lid portion 453a, 453b is opened, the corresponding seal member 440 will be presented for use with opening 440 facing upward, as described in additional detail below. It should be understood that in the illustrated embodiment, packaging 450 may store two identical seal members 440, with one of the seal members 440 being a spare part available for use if necessary. Packaging 450 could maintain a similar design but be altered to hold one, or more than two, seal members 440 or other single-use components. Preferably, for each component packaged in packaging 450, an individual corresponding lid is provided so that any component may be accessed while the remaining components remain secure and sterile within packaging 450.

Figure 4A:
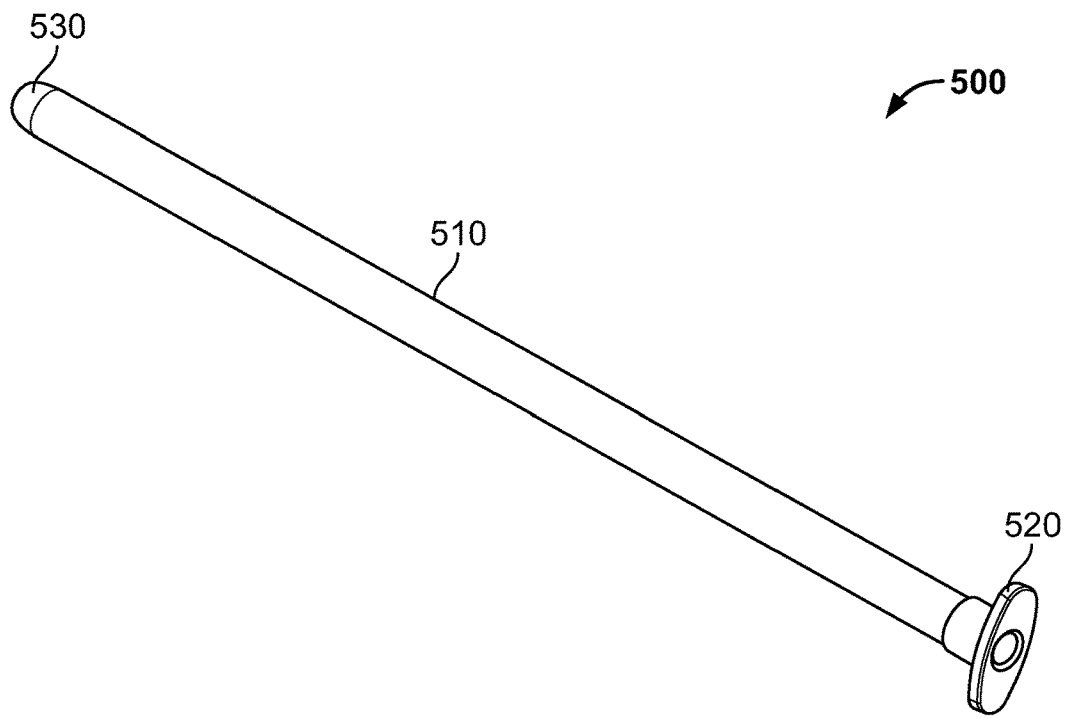

Delivery tube subassembly 500 is illustrated in FIGS. 4A-D. Generally, delivery tube subassembly 500 includes a graft tube or cannula 510. Cannula 510 may include a generally hollow cylindrical body extending from a proximal end to a distal end. The proximal end may include a flange member 520 including two extension members extending a length radially outwardly from the body of cannula 510 a distance greater than the diameter of the main body. A center portion of the flange member 520 may include an aperture leading into the main body of cannula 510. Flange member 520 and cannula 510 may be formed integrally, or may be coupled together in any suitable fashion. The distal end of cannula 510 may include a slight inward taper 530. Additional views of delivery tube assembly 500 and portions thereof are shown in FIGS. 4B-D.

As shown in FIG. 4B, the main body of cannula 510 preferably includes indicia to mark volume or other values. For example, hash marks to indicate a volume up to 5 cubic centimeters ("cc") in 1 cc increments may be provided. Preferably, cannula 510 is formed of a transparent material or other material that allows a user to see the contents inside cannula 510. For example, cannula 510 (as well as flange 520) may be formed of polycarbonate or similar materials, with the delivery tube subassembly 500 provided sterile with the intent to dispose the delivery tube subassembly 500 after a single use. One or more radiopaque stripes may be provided along substantially the entire length of cannula 510 so that cannula 510 may be more easily visible, for example under fluoroscopy. In one embodiment, two stripes are provided in diametrically opposed positions along the length of cannula 510, with the radiopaque stripes being formed of barium sulfate impregnated into the polycarbonate material forming cannula 510. Although the particular dimensions of components of delivery tube subassembly 500 may depend on the particular intended use, cannula 510 preferably has an inner diameter of between about 5 mm and about 7 mm, most preferably about 6 mm.

Flange 520 is shown isolated in FIG. 4C. Flange 520 includes two symmetrical wings that extend from the aperture leading into the interior of cannula 510. Each of the wings may have a maximum length that is approximately equal to the diameter of the aperture between the two wings, although other geometries and sizes may be appropriate. As is explained in greater detail below, flange 520 may be used in to lock the delivery tube subassembly 500 into a loading funnel 600 in order to facilitate loading bone graft into the cannula 510 prior to delivery of the bone graft to a patient. The taper 530 at the distal end of cannula 510 is shown in FIG. 4D in cross-section. As can be seen, although the exterior of cannula 510 is tapered inwardly, the interior of cannula 510 at the distal end need not have any corresponding taper.

Figure 5A:
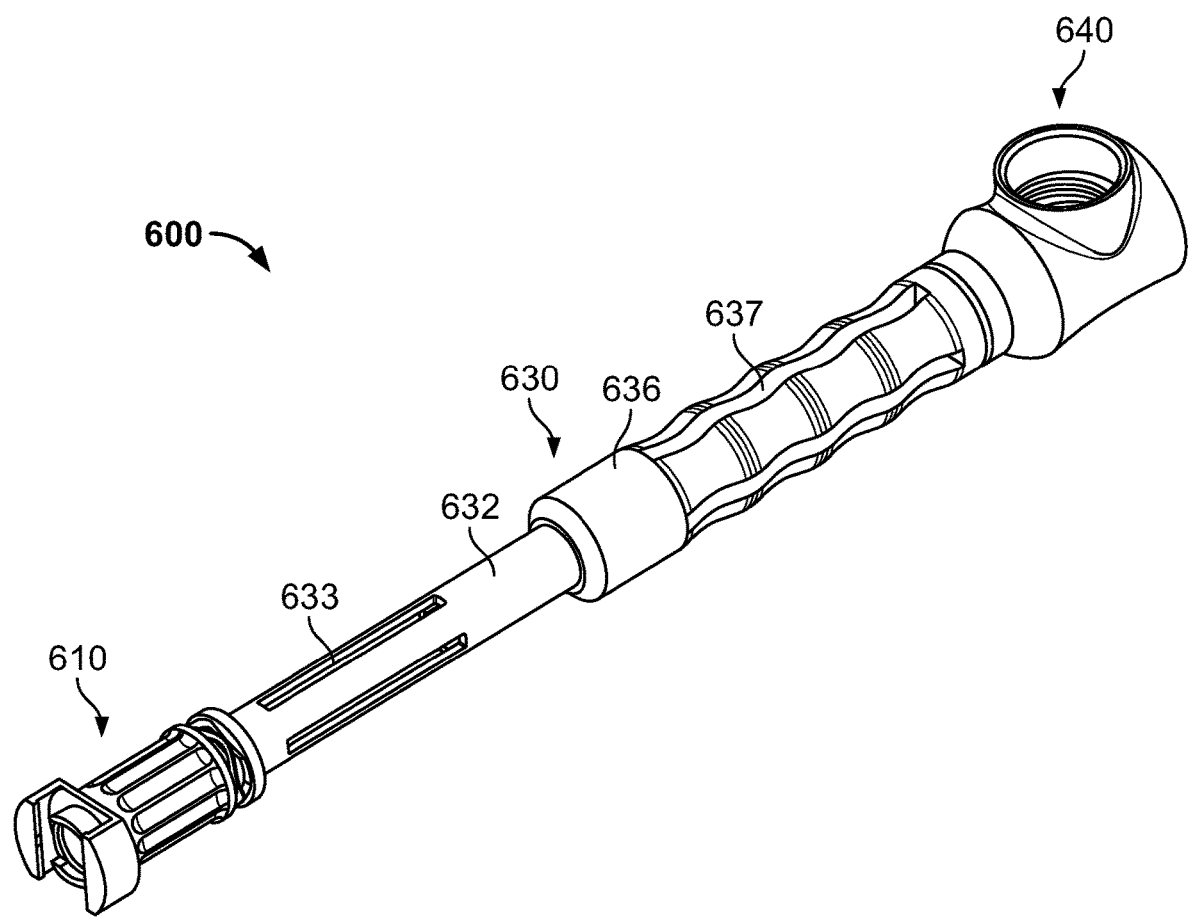

A loading funnel 600 to assist loading the delivery tube subassembly 500 is illustrated in FIG. 5A. Loading funnel 600 may take the general form of an elongated cylinder or tube with a number of features that facilitate moving bone graft from a first source into the delivery tube subassembly 500. For example, loading funnel 600 has a first cannula docking end 610, a center body portion 630 extending from the cannula docking end, and a second syringe docking end 640 opposite the cannula docking end 610. Each section is described in more detail below. Preferably, loading funnel 600 is formed of a metal suitable for use in surgery, with the loading funnel being sterilizable and intended for reuse.

Figure 5B:
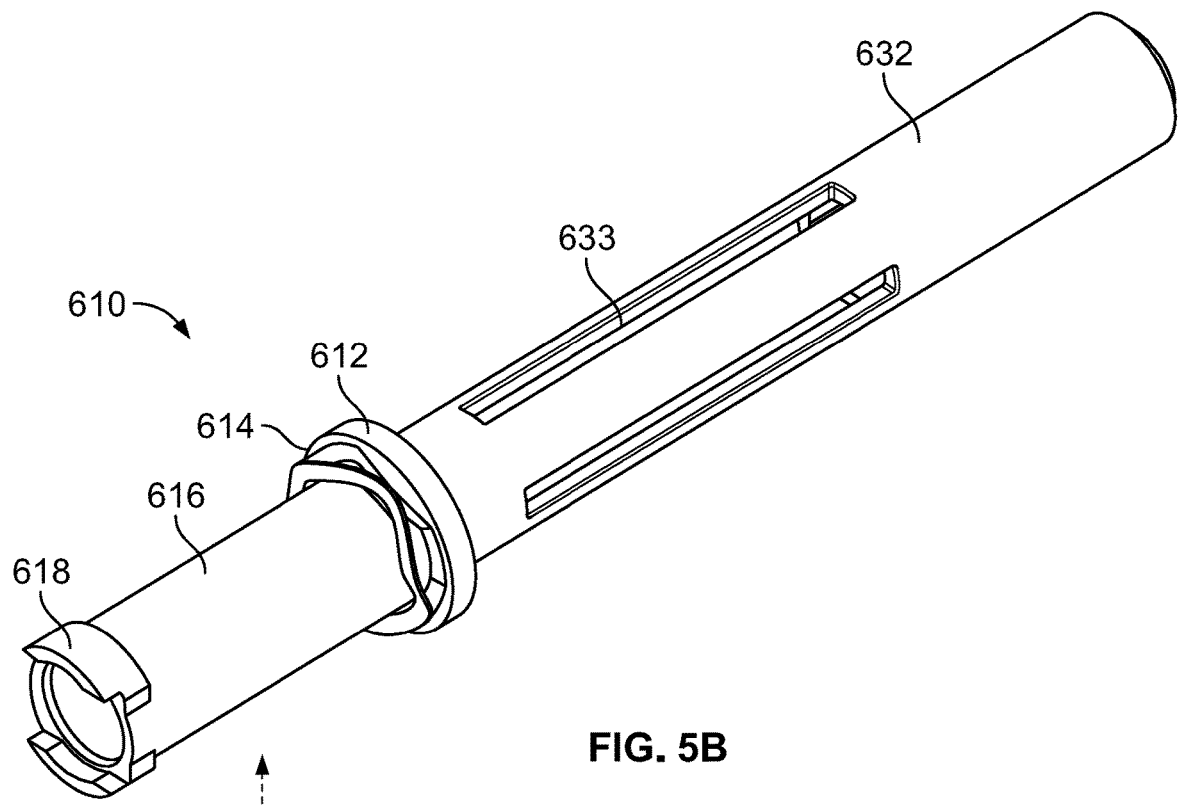
Figure 5C:
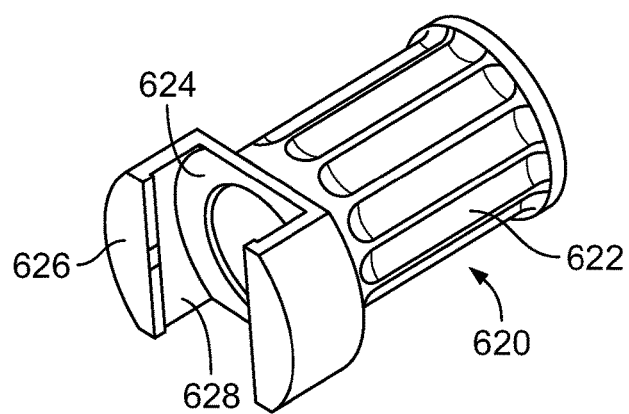

Cannula docking end 610 of loading funnel 600 is illustrated in a partially disassembled state in FIG. 5B with a locking hub member 620, which is shown in FIG. 5C, removed therefrom. Cannula docking end 610 of loading funnel 600 may be separated from a first end 632 of center body portion 630 by a flange 612. Flange 612 may take the form of a circular member integrally formed or otherwise coupled to tube 616 of cannula docking end 610, which may be integral with the first end 632 of center body portion 630, with the flange 612 extending radially outward of the tube. Flange 612 may provide a contact point for a spring 614, which as illustrated takes the form of a wave spring. The terminal end of cannula docking end 610 may include two diametrically opposed extensions 618. As described in greater detail below, the extensions 618 may be shaped and dimensioned so that the flange 520 of delivery tube subassembly 500 mates or otherwise locks or couples with extensions 618 in only two orientations. Extensions 618 may also extend radially outward of tube 616 to provide a surface for locking hub 620, described below, to abut.

Locking hub 620 may include a substantially cylindrical body portion 622 with a hollow cylindrical center adapted to fit over tube 616 of cannula docking end 610. Locking hub 620 may be rotatable with respect to tube 616, with a plurality of grooves or other friction members or other grip members provided to facilitate a user in rotating locking hub 620. One end of locking hub 620, when assembled on tube 616, may abut spring 614. The other end of locking hub 620 may include a flat face 624 adapted to abut extensions 618. When locking hub 620 is assembled to tube 616 with face 624 abutting extensions 618, spring 614 may be in a compressed state so that a continuous force is applied to locking hub 620, pushing locking hub 620 against extensions 618. With this configuration, friction may be created or provided so that locking hub 620 is unlikely to rotate with respect to tube 616 in the absence of intentionally applied rotational forces. Two extensions 626 may extend both radially outwardly and axially away from face 624, each extension 626 including a recess 628 that has a substantially arcuate shape. The arcuate shape of recesses 628 may correspond to the shape of the wings of the flange 520 of cannula 510. With this configuration, as is described in additional detail below, flange 520 may be positioned between extensions 618 while extensions 626 substantially align with extensions 618. Then, locking hub 620 may be rotated approximately ninety degrees clockwise or counterclockwise until extensions 626 are staggered with respect to extensions 618. In this rotated position, the wings of the flange 520 of cannula 510 may be positioned within recesses 628 formed by extensions 626, with the flange 520 being effectively locked in place because the wings of flange 520 are too large to clear the extensions 626 if the flange 520 is pulled out of the loading funnel 600.

Syringe docking end 640 of loading funnel 600 is illustrated in a partially isolated state in FIG. 5D, with a transfer hub member 650 shown fully isolated in FIGS. 5E-F. Second end of 636 of center body portion 630 may extend from the first end 632 and join transfer hub member 650, for example by being coupled or integrally formed therewith. Transfer hub member 650 may include a syringe dock 652. Syringe dock 652 may include a substantially cylindrical wall defining a recess having a longitudinal axis that is orthogonal to the main longitudinal axis of docking funnel 600. Syringe dock 652 may include mating features, such as internal threads, to mate with corresponding external threads 750 of a syringe member 700, described in greater detail below. The syringe dock 652 leads into a holding area 654. As is described below, once syringe member 700 is coupled to syringe dock 652, a user may advance bone graft into the holding area 654.

A face 656 of transfer hub member 650 may have a concave profile as best seen in FIG. 5E. Once bone graft has entered into holding area 654, a user may advance a loading tool 800, described in greater detail below, into holding area 654 to advance bone graft through an aperture 658 in transfer hub member 650. The distal end 530 of cannula 510 may be positioned adjacent aperture 658 when cannula 510 is assembled within loading funnel 600, so that bone graft in holding area 654 may be advanced into cannula 510. Preferably, the diameter of aperture 658 is slightly smaller than the inner diameter of cannula 510 to help facilitate bone graft transferring through the aperture 658 into cannula 510. For example, if the inner diameter of the cannula is about 6 mm, aperture 658 preferably has a diameter of between about 5.5 mm and about 6 mm, most preferably about 5.7 mm and about 5.8 mm. The concave profile of face 656 may facilitate in guiding the loading tool 800 into holding area 654.

Referring again to FIG. 5A, the center body portion 630 of loading funnel 600 may be substantially cylindrical, including a first end 632 and a second end 636. The first end 632 may include a plurality of slots 633 extending along a portion of the length thereof, which may be spaced evenly around the circumference of first end 632. Similarly, the second end 636 may include a plurality of slots 637 extending along a portion of the length thereof, which may be also be spaced evenly around the circumference of second end 636. In the illustrated embodiment, the first end 632 and second end 636 each include four slots 633, 637. Whether formed integrally or joined together, a continuous passageway may be formed along the length of both first end 632 and second end 636, the passageway sized and shaped to receive cannula 510 therethrough. As described in greater detail below, the slots 633 and 637 may lead into the passageway so that a user can view indicia on cannula 510 while loading the cannula 510. The slots 633 and 637 may also provide for weight reduction of loading funnel 600. One or both of the first end 632 and second end 636 may include features, such as ridges in second end 636, to facilitate a user in gripping that portion of the loading funnel 600.

Figure 6A:
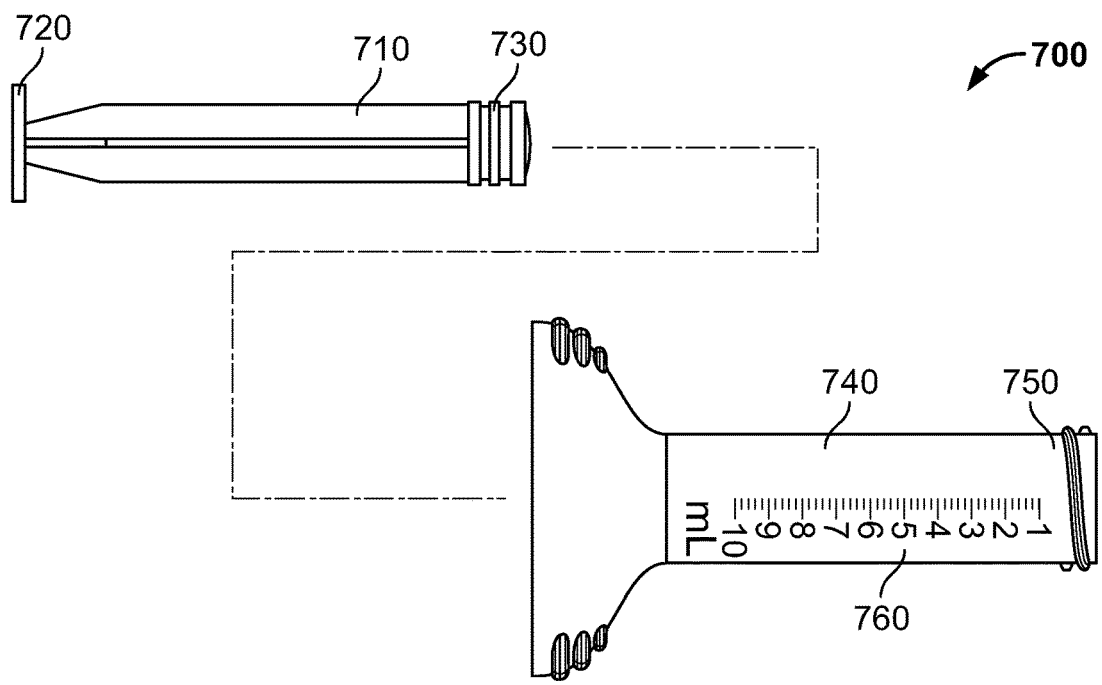
FIGS. 6A-B are various views of a syringe assembly according to an embodiment of the disclosure.
Figure 6B:
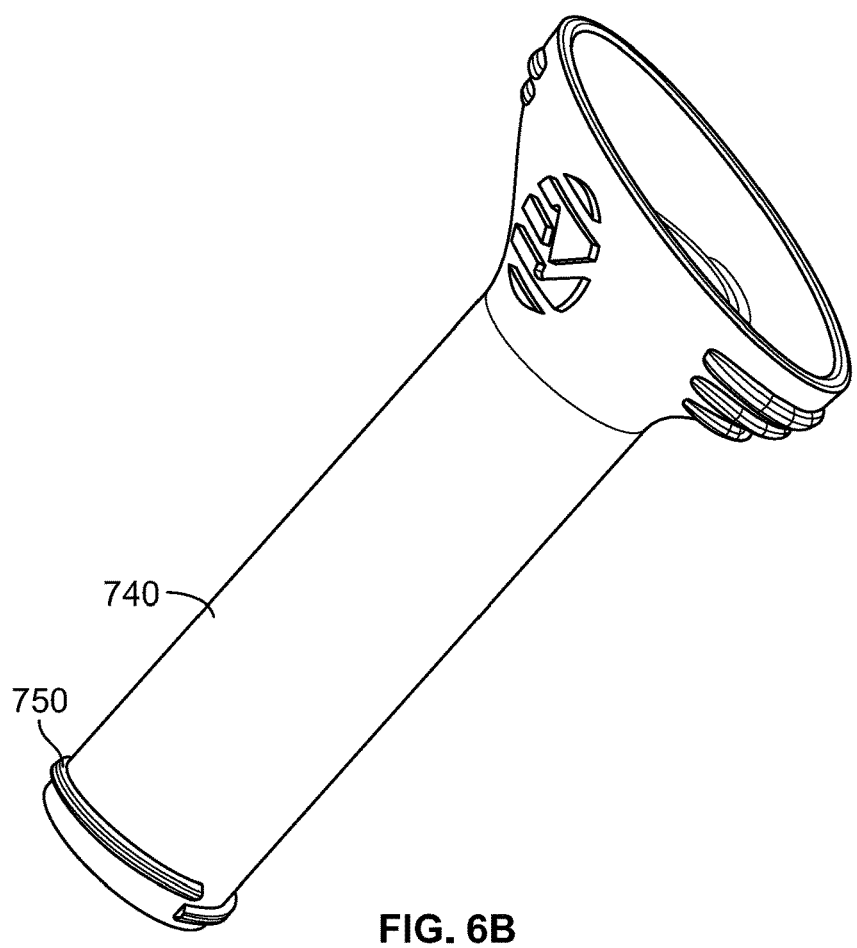

Syringe member 700 is illustrated in FIGS. 6A-B. The components of syringe member 700 may be formed of material intended for a single use and to be disposable, such as a clear plastic material such as polycarbonate. As shown in FIG. 6A, syringe member 700 may include a plunger member and a housing member. The plunger member may include a shaft 710 with a grip member 720, which may take the form of a substantially flat surface, at a proximal end of the shaft 710, and a seal 730 at a distal end of the shaft 710. The plunger fits snugly within a shaft 740 of the housing, which may be substantially cylindrical and hollow, preferably with the seal 730 forming an airtight seal with the shaft 740 of the housing. In some embodiments, seal 730 may be formed of a rubber or another elastomeric material to help facilitate the formation of an airtight or substantially airtight seal. Mating features such as external threads 750 may be formed on a distal end of the shaft 740, the external threads 750 corresponding to the internal threads of the syringe dock 652 of loading funnel 600. Shaft 740 also preferably includes indicia 760 which may be hash marks to indicate some quantity, such as volume of bone graft loaded into the syringe member 700. As noted above, shaft 740 is preferably translucent so that the contents of syringe member 700 may be easily seen and compared with indicia 760.

Figure 7B:
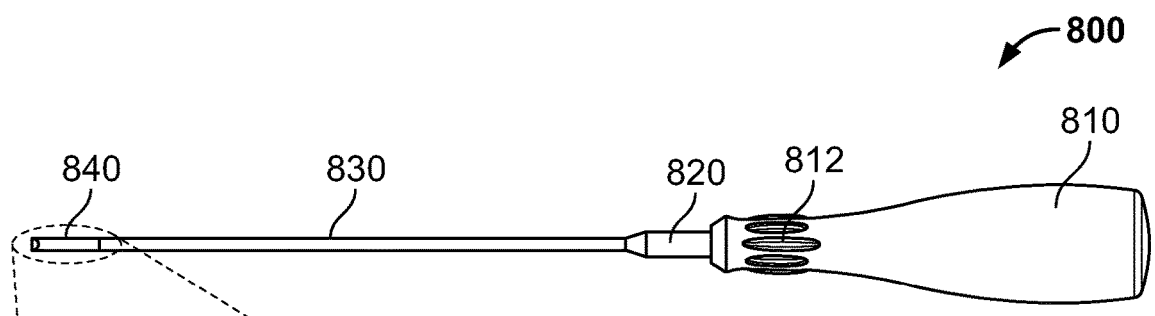
Figure 7C:
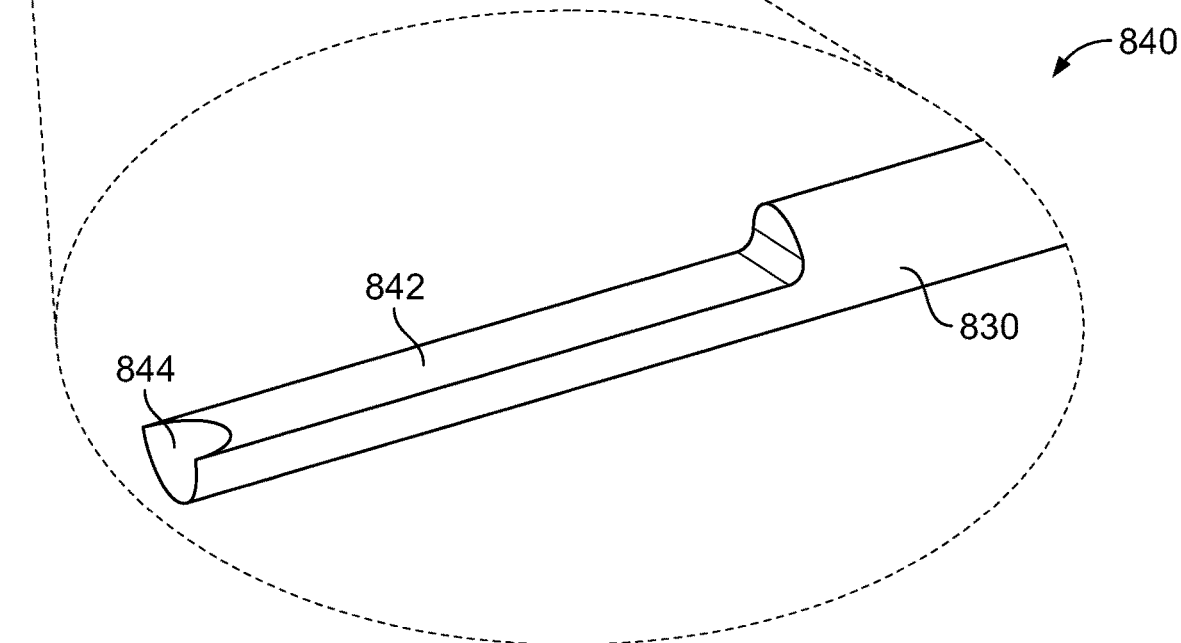

A loading tool 800 for use in driving bone graft from holding area 654 into cannula 510 is illustrated in FIGS. 7A-C. Loading tool 800 may include a handle 810, shaft members 820, 830, and a distal tip 840. Handle 810 may be formed from a material suitable for use in surgery, including metal or rubber that provides a suitable grip, preferably where the material may be sterilized and reused. Handle 810 may have a rounded proximal end that transitions into a narrow rounded distal end. Preferably, handle 810 does not include any substantially flat surfaces, which may facilitate a user in gripping handle 810 using different grip configurations. The distal end of handle 810 may include texturized surfaces such as ridges 812, which may facilitate the user's grip on handle 810. Shaft 820 may extend into handle 810 and be securely coupled thereto. Shaft 820 may transition into a narrow substantially cylindrical shaft 830, which itself may transition into distal tip 840. Shafts 820, 830 and distal tip 830 may be formed as a unitary piece of material and may be formed from metal or other material suitable for surgery, particularly materials that may be sterilized so that loading tool 800 may be reused in different procedures. As best seen in FIG. 7C, the distal tip 840 may be substantially in the shape of a half-cylinder 842 which may be approximately half the size of the cylindrical shaft 830. The distalmost end of distal tip 840 may have a concave recess 844 in the shape of a part of a sphere or other similar shape. The shape of the distal tip 840 may provide extra flexibility for the user in terms of the user's ability to pack bone graft from holding area 654 into cannula 510. Shaft member 830 may have a diameter of between about 2 mm and 4 mm, most preferably about 3 mm. Tip 840 may be about half the size of shaft member 830. Preferably, the diameter of shaft 830 is small enough compared to the inner diameter of cannula 510 so that space is available between the shaft 830 and the cannula 510 when the shaft 830 is inside the cannula 510, which may facilitate better manipulation and placement of bone graft during the loading of cannula 510. The use all of the above components, including loading tool 800, to load cannula 510 with bone graft is discussed in greater detail below.

Figure 8:
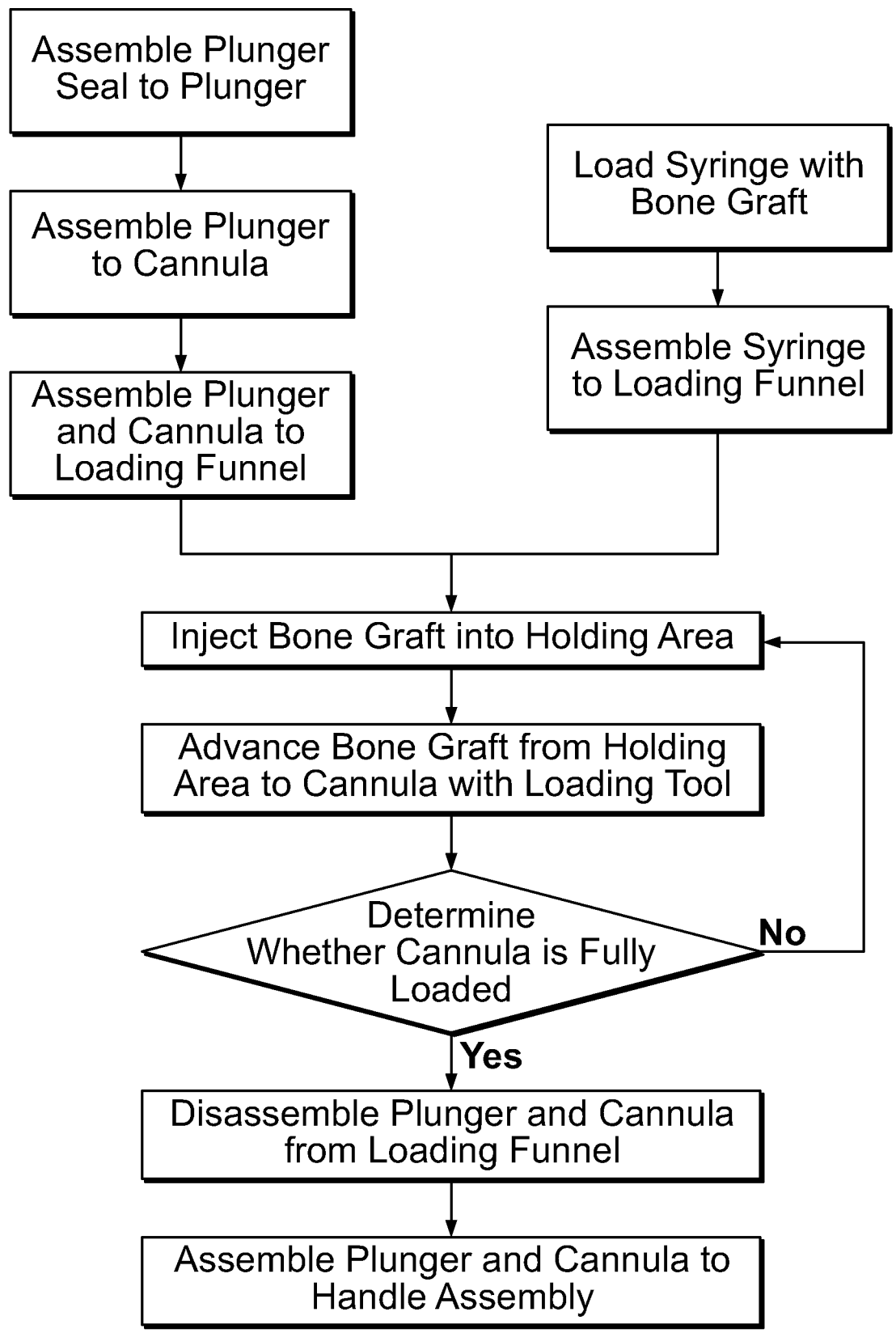
FIG. 8 is a flowchart of a method of loading bone graft into a delivery tool according to an embodiment of the disclosure.
Figure 9A:
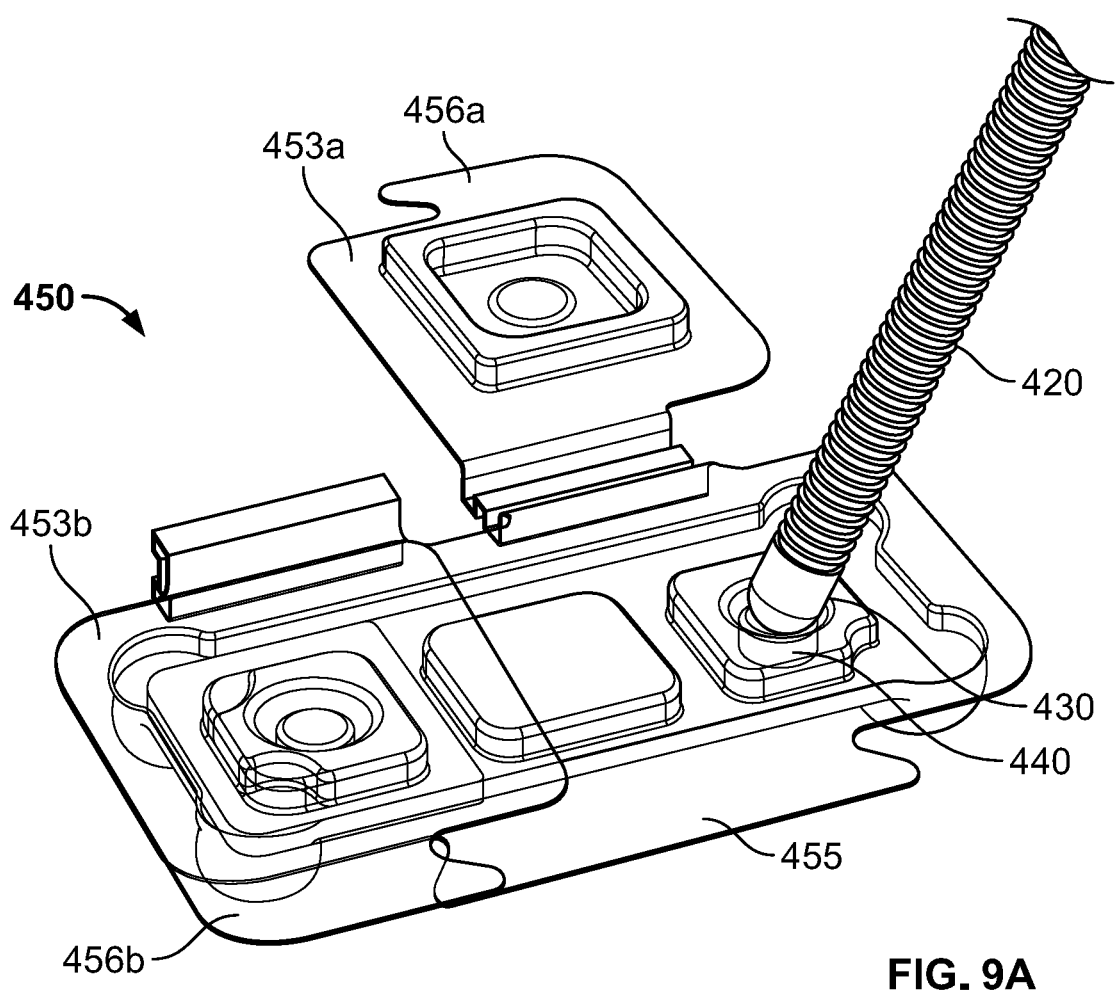
FIGS. 9A-G are various views of steps of the flowchart of FIG. 8.
Figure 9B:
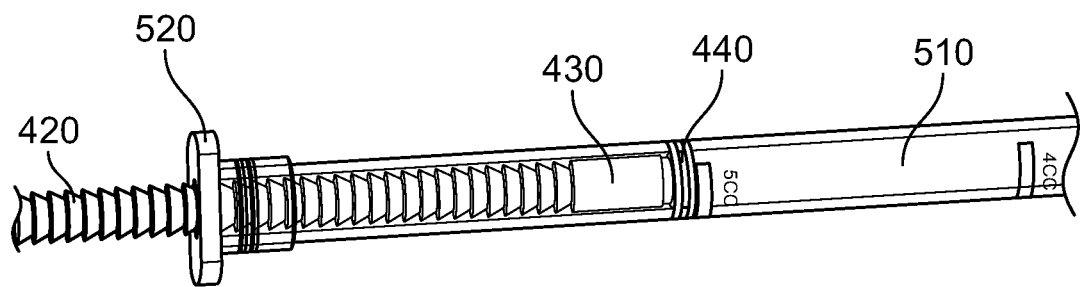
Figure 9C:
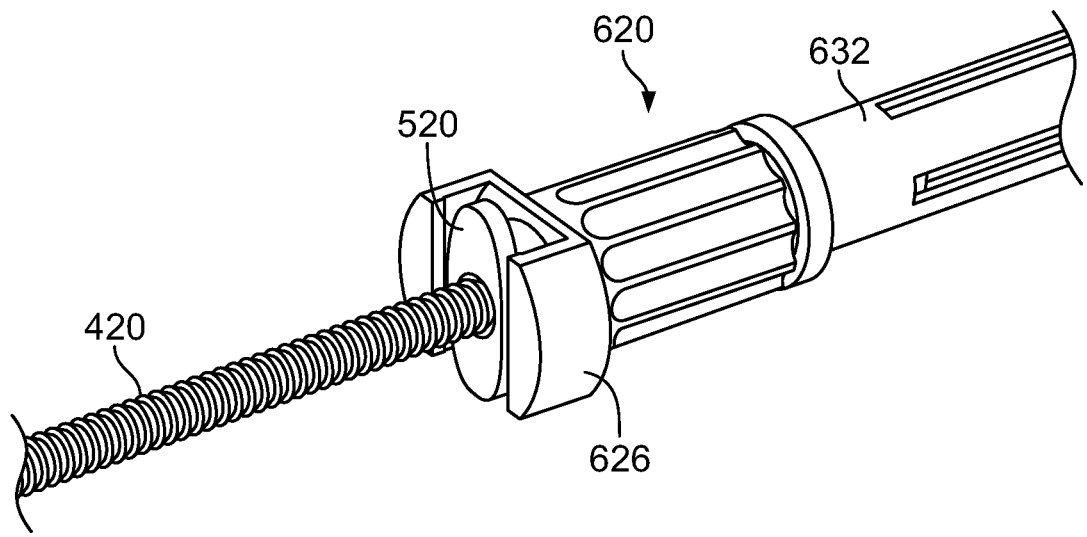
Figure 9D:
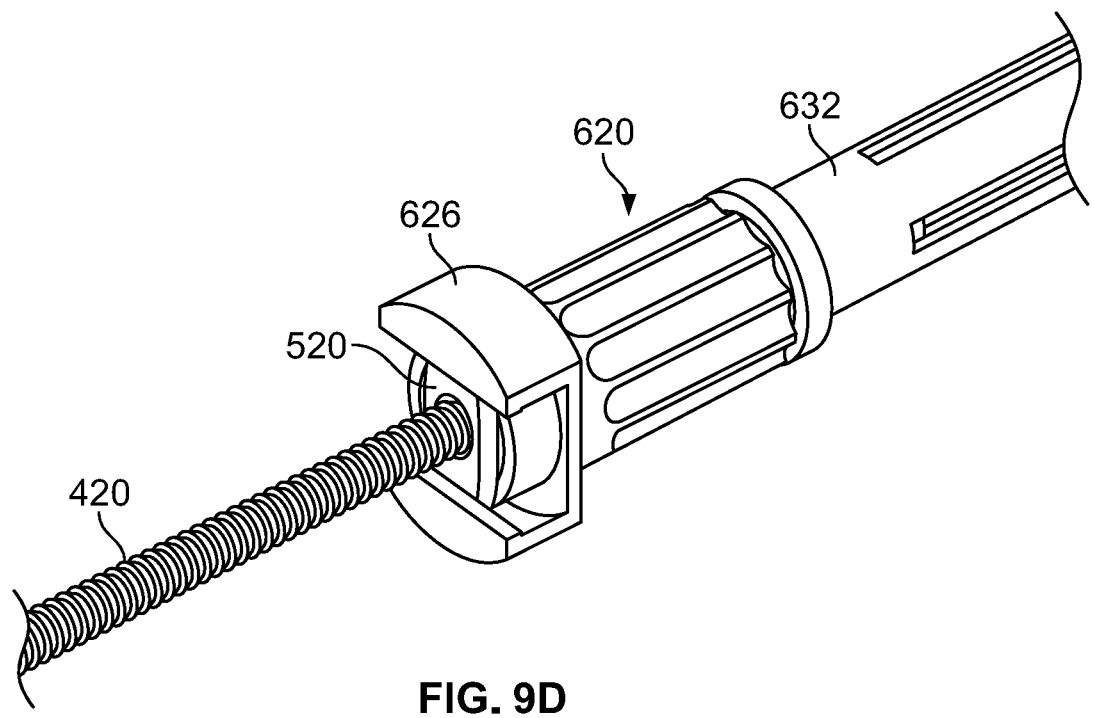

A flowchart illustrating a method of loading the delivery tube subassembly is provided in FIG. 8. In a first step, the plunger subassembly 400 may be taken, for example from a container containing re-usable sterilized instruments, and the distal tip 430 may be pressed onto plunger seal 440, which itself may be taken from a separate container of disposable components, as shown in FIG. 9A. Then, the plunger subassembly 400 may be inserted into the delivery tube subassembly 500, with the leading end with seal 440 inserted through the aperture in the flange 520 of delivery tube subassembly 500, as shown in FIG. 9B. The delivery tube subassembly 500 may be provided in container or as part of the same kit as the seal 440. The seal 440 preferably forms a fluid tight and/or air tight seal with cannula 510. The distal face of seal 440 should be inserted to a position within cannula 510 based on the amount of volume of bone graft that the user desires to load into cannula 510. For example, if the surgical procedure calls for loading 5 cc of bone graft into the cannula 510, the distal face of seal 440 should be inserted to the hash mark on cannula 510 indicating 5 cc. As noted above, the cannula 510 is preferably translucent to facilitate this positioning. The tight fit between cannula 510 and seal 440 facilitates the user handling the assembled items without worrying that the position of seal 440 with respect to cannula 510 will shift without intentional force applied to change the position of seal 440. With the distal face of seal 440 in the desired position and the cannula 510 friction fit with the plunger subassembly 400, the user then inserts the assembled components into the cannula docking end 610 of loading funnel 600. The length of cannula 510 is sized so that as the distal end 530 of cannula 510 becomes adjacent the aperture 658 in transfer hub member 650, the flange 530 of cannula 510 makes contact with the flat face 624 of locking hub 620, with the flange 530 positioned between extensions 618 of cannula docking end 610, as shown in FIG. 9C. Then, the user rotates locking hub 620 approximately 90 degrees clockwise and counterclockwise, until the wings of flange 520 are positioned between the flat face 624 and extensions 626 of cannula docking end 610, as shown in FIG. 9D. In this condition, the plunger subassembly 400 and delivery tube subassembly 500 are in a locked position with respect to loading funnel 600. In an embodiment in which cannula 510 includes hash marks of 1 cc, 2 cc, 3 cc, 4 cc, and 5 cc, the 4 cc and 5 cc indicia may be visible through slots 633, with the 2 cc and 3 cc indicia visible through slots 637, although other configurations are possible.

Figure 9E:
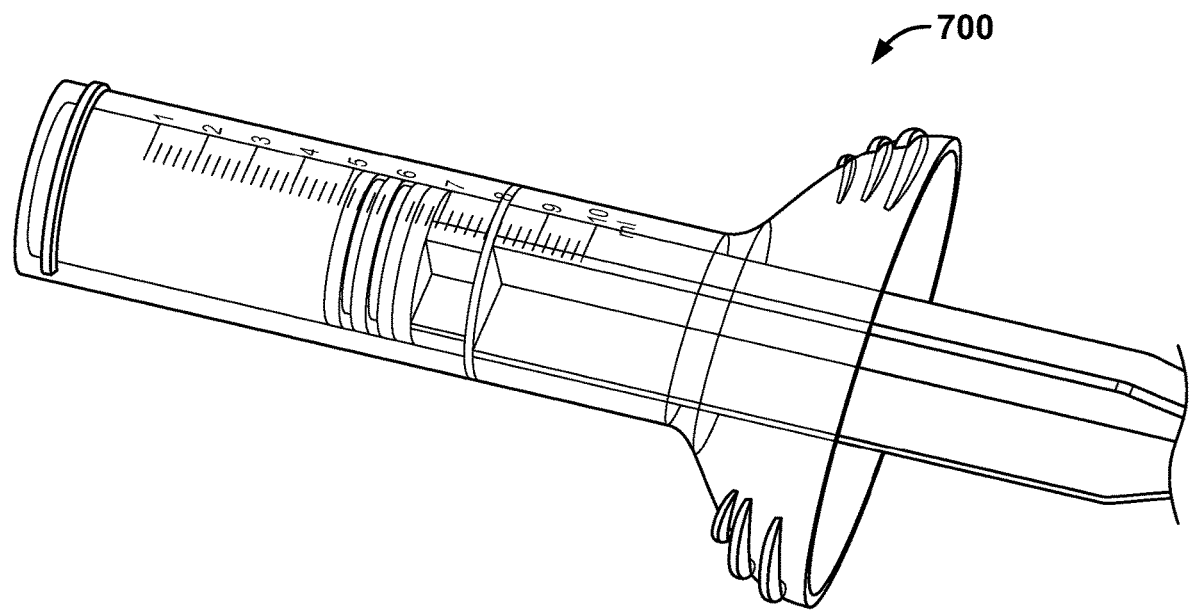
Figure 9F:
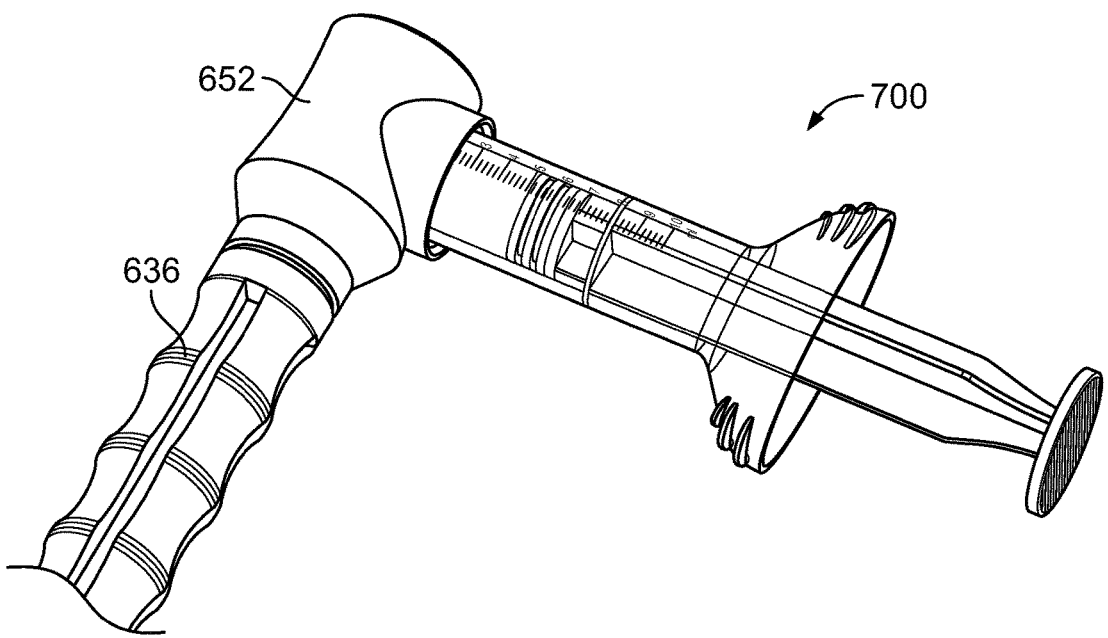

In a separate group of steps, which may occur in any time relation with respect to the three described in the paragraph above, the user loads bone graft into the shaft 740 of string member 700 and couples the syringe member 700 to the loading funnel 600. One example of a suitable bone graft substitute material may be Vitoss® Bone Graft Substitute, Vitoss® Bioactive Foam Back Bone Graft Substitute, or other products in the Vitoss® line sold by Stryker Corp. Examples of suitable bone graft materials are described in greater detail in U.S. Pat. Nos. 7,534,451, 6,383,519 and 6,521,246 and in U.S. Patent Publication No. 2005/0288795, the disclosures of which are both hereby incorporated by reference herein. The bone graft may be packed into the shaft 740 of syringe member 700 by hand or other suitable method to a desired volume. For example, if 5 cc of bone graft is desired, the seal 730 of syringe member 700 may be advanced to the corresponding 5 cc (or 5 mL) hash mark on the indicia 760 of shaft 740, as shown in FIG. 9E. As noted above, shaft 740 is preferably translucent so that a user can easily confirm the position of the seal 740. The user then may hand pack bone graft to fill shaft 740. Although a significant benefit of the system described herein is the capability of a user to use any desired bone graft material in syringe member 700, as opposed to providing a pre-packed syringe, in some embodiments a syringe pre-packed with bone graft may be provided with the system. Once the syringe member 700 is loaded, the user may couple the mating features 750 of syringe member 700 with the corresponding mating features in syringe dock 652, for example by screwing threads of the syringe member 700 to corresponding threads of syringe dock 652, as shown in FIG. 9F. The connection between syringe member 700 and syringe dock 652 may be airtight or substantially airtight. This seal, as well as the seal between seal 440 and cannula 510, may be particularly helpful when the bone graft material has a liquid component that might otherwise leak out of a non-sealed portion of the system. Although it was noted above that the first five steps described above may be completed in any order, it is preferable that the plunger 400 and cannula 510 are assembled to the loading funnel 600 prior to the loaded syringe member 700 being coupled to the loading funnel 600, so that upon connection of the loaded syringe member 700 to the loading funnel 600, the cannula 510 is immediately ready to be loaded.

Figure 9G:
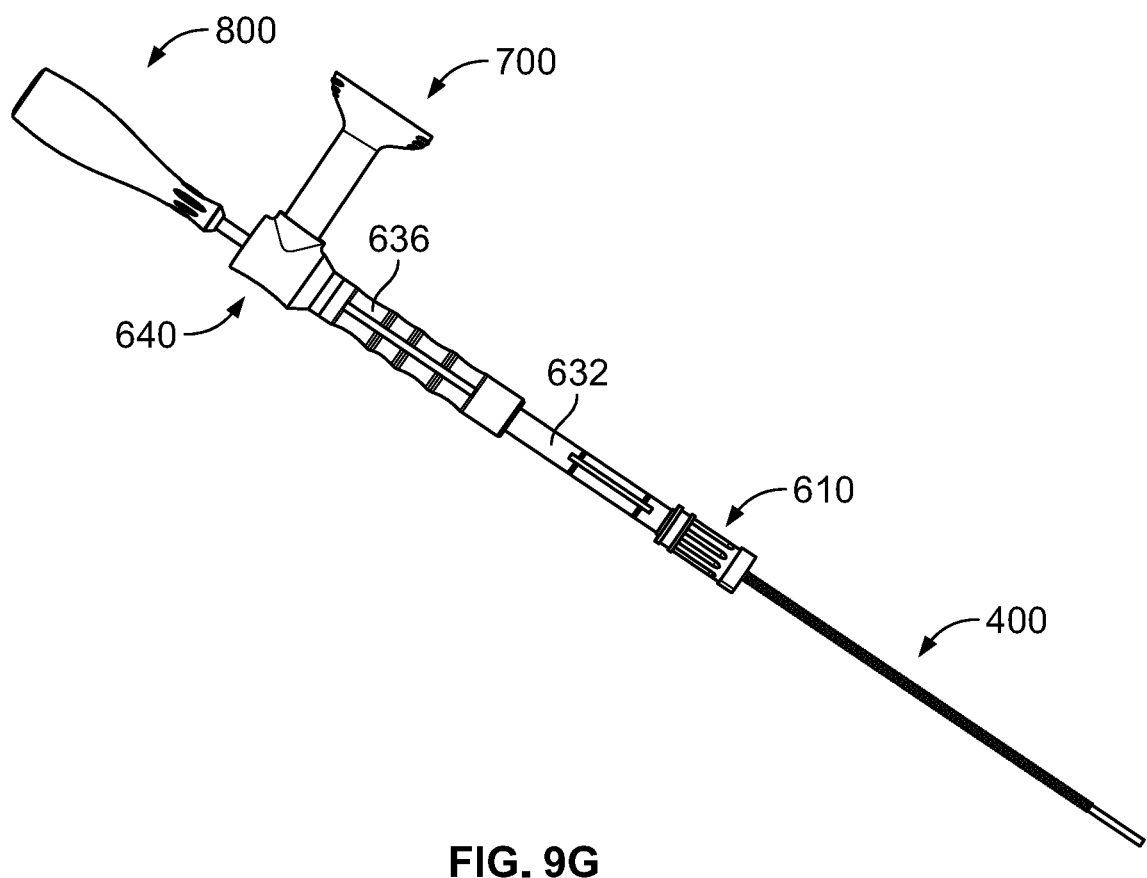

With the loaded syringe member 600 and the plunger 400 and cannula 510 coupled to loading funnel 600, the user may begin loading the cannula 510. In order to load the cannula 510, the user first fills at least a portion of holding area 654 with bone graft by advancing the shaft 710 of syringe member 700 distally. Once the user visually confirms that a suitable amount of bone graft is positioned within holding area 654, the user may advance the distal tip 840 and shaft 830 of loading tool 800 through the holding area 654, through the adjacent aperture 658, and into cannula 510, pushing at least some bone graft from the holding area 654 into the cannula 510 as shown in FIG. 9G. Preferably, the user initially advances the bone graft to a position adjacent the seal 440 of plunger subassembly 400. The user may then determine whether the cannula 510 is fully loaded with bone graft. If the cannula 510 is not fully loaded, the user may remove loading tool 800, advance the shaft 710 of syringe member 700 to once again fill holding area 654 with bone graft, and then using the loading tool 800 to further fill cannula 510. The user may iteratively repeat this process until the cannula 510 is fully loaded with bone graft with the desired volume. Preferably, pieces of the bone graft are all smaller than about 5 mm, particularly if cannula 510 has an inner diameter of about 6 mm.

The recess 844 of the loading tool 800 may provide the user the capability of scooping, cutting, breaking, or otherwise easily manipulating the bone graft material during loading of the cannula 510. Similarly, the substantially half-cylinder 842 of distal tip 840 may provide additional capability for the user to position the bone graft as desired. In other words, these varied shapes may provide additional maneuverability and control for the user compared to a loading tool that is solely formed as a cylinder.

Figure 10:
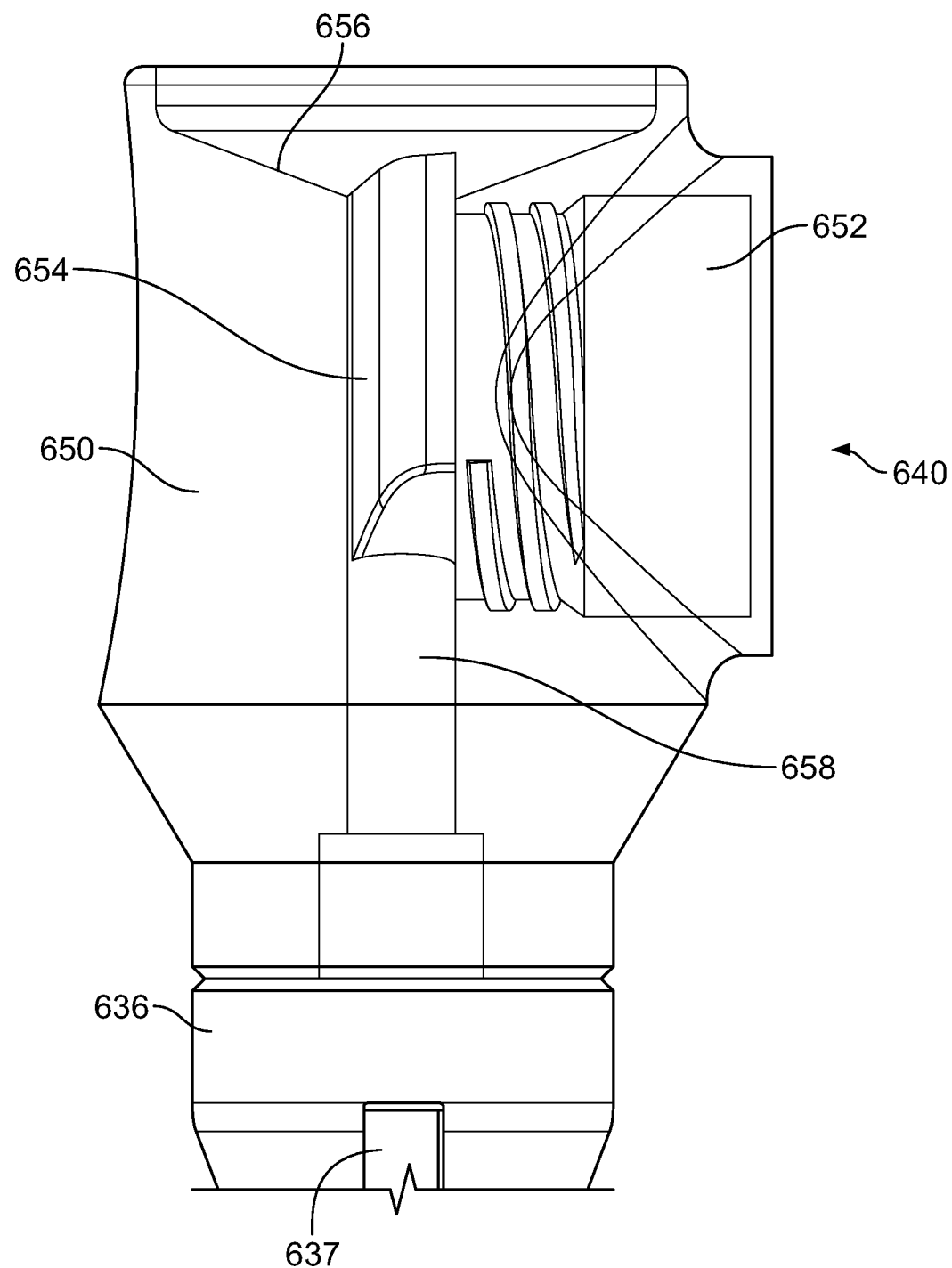
FIG. 10 is a partially transparent view of a syringe docking end of the loading funnel of FIGS. 5A-F.

The configuration above provides a number of additional benefits not already noted. For example, referring to the partially transparent view of syringe docking end 640 in FIG. 10, it can be seen that the syringe member 700 is capable of advancing bone graft into holding area 654 without any significant amount of tapering. In particular, the syringe member 700 itself does not have a significant taper in the distal end of shaft 740. In addition, the holding area 654, as best seen in FIG. 5F, is shaped so that at the point where the distal end of syringe member 700 is adjacent holding area 654, there is not a significant taper at the transition point. Many bone graft materials behave, at least in part, as non-Newtonian fluids that vary in viscosity depending on hydraulic forces and time. Because of this, as bone graft is pushed through a tube, pressure may build causing difficulty in moving the bone graft to the intended position. This problem may be amplified when the geometry of the tube which the bone graft is moving begins to taper or otherwise narrow. The geometry of syringe member 700 as well as the transition from syringe member 700 to holding area 654 helps avoid this problem because the bone graft does not encounter any significant taper, and further because there is a very short stroke required to move the bone graft from the distal end of the syringe member 700 into the holding area 654. These features may make the loading process significantly easier than in prior systems.

Other benefits may be provided by the "L" shaped loading configuration described above. More particularly, as noted above and best seen in FIG. 9G, when the syringe member 700 and the cannula 510 are assembled to the loading funnel 600, the main longitudinal axis of syringe member 700 is substantially orthogonal to the main longitudinal axis of cannula 510. This further facilitates a short stroke of the syringe member 700 to move the bone graft in a first direction into the holding area 654, with that small amount of material then moved along a substantially orthogonal axis into cannula 510 using loading tool 800. This configuration allows for an easier and more easily controlled loading of cannula 510 than, for example, if the entire loading from a syringe to a delivery cannula was along a single axis.

Referring again to FIG. 8, once the user determines that the cannula 510 is loaded with the desired volume of bone graft, the user may remove the loading tool 800 and then rotate locking hub 620 approximately ninety degrees in either the clockwise or counterclockwise direction to unlock the flange 520 of cannula 510 from loading funnel 600. In the unlocked condition, the cannula 510 and the plunger subassembly 400 may both be removed from the loading funnel 600. The assembled cannula 510 and plunger 400 may then be coupled to handle subassembly 200. Referring back to FIG. 2A, one of the wings of the flange 520 of cannula 510 is snapped or otherwise coupled to the corresponding slot of second retaining feature 250. Similarly, a portion of the shaft 420 of plunger subassembly 400 extending beyond the flange 520 may be snapped or otherwise coupled to first retaining feature 240. In this position, the distal face of pawl 320 is positioned between two adjacent teeth 422 of shaft 420. Once in the fully assembled condition shown in FIG. 1, the user may advance the distal tip of 530 of cannula 510 to the desired position in the patient's body. Bone graft may be ejected from the distal tip 530 of cannula 510 by squeezing moving handle 220 toward fixed handle 210, causing pawl 320 to push the shaft 420 of plunger 400 distally with respect to cannula 510. The user may then relax the grip on moving handle 220, and repeat the process to iteratively and incrementally expel bone graft from the distal tip 530 of cannula 510 into the desired location in the patient. The user may continue to advance plunger 400 distally until the pawl 320 is adjacent the proximal portion 410 of the plunger 400 which contains no teeth as a safety feature. At this point, the user can no longer advance plunger 400 by squeezing handles 220 and 210, helping to ensure the user cannot unintentionally advance the plunger 400 through the cannula 510 and into the surgical site.

Once the user expels the desired amount of bone graft from cannula 510, the assembly may be removed from the patient and the surgical procedure completed as desired. In order to disassemble the cannula 510 and plunger 400 from handle subassembly 200, the user may lay the handle subassembly on a flat surface, such as a surgical table or accessory table, with the open ends of retaining features 240, 250 facing away from the surface of the table. In this position, the wing of flange 520 extending through the slot of second retaining feature 250 contacts the surface of the table, with the second retaining feature 250 remaining spaced from the table. The user can then press the handle subassembly 200 forcefully toward the table, causing a corresponding force to push the wing of flange 520 contacting the table away from the table, causing the cannula 510 and plunger 400 to dislodge from the handle subassembly. Any disposable components, such as the delivery tube subassembly 500, the seal 440 of plunger subassembly 400, and the syringe member 400 may all be discarded. Any reusable portions, such as the remaining portions of plunger subassembly 400, the loading funnel 600, the handle subassembly 200, and the loading tool 800, may then be sterilized for use in another procedure. Although the assembly disclosed herein may be used in any desired surgical procedure, it may be particularly useful for use in facet joints of the spine or for delivery into the intervertebral space, similar to procedures described in greater detail in the '352 Publication.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, one embodiment of an assembly or subassembly described above may be combined with other embodiments of assemblies or subassemblies described above.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of loading bone graft into a bone graft delivery system, the method comprising:
coupling a container having the bone graft therein to a loading member so that a longitudinal axis of the container is transverse to a longitudinal axis of the loading member;
positioning a cannula within a passageway of the loading member so that a longitudinal axis of the cannula is parallel to the longitudinal axis of the loading member;
advancing a first amount of the bone graft from the container to the loading member; and
inserting a loading tool into an interior space of the loading member to advance at least a portion of the first amount of bone graft from the interior space of the loading member into the cannula.

2. The method of claim 1, further comprising:
after advancing the portion of the first amount of bone graft into the cannula, advancing a second amount of the bone graft from the container to the loading member; and
inserting the loading tool into the interior space of the loading member to advance at least a portion of the second amount of bone graft from the interior space of the loading member into the cannula.

3. The method of claim 1, wherein the container is a syringe member.

4. The method of claim 3, wherein coupling the container to the loading member includes threading a threaded portion of the syringe member into a threaded docking portion of the loading member.

5. The method of claim 1, further comprising inserting a plunger member into an interior space of the cannula prior to positioning the cannula within the passageway of the loading member.

6. The method of claim 5, further comprising:
removing the cannula from the loading member while the plunger member is still within the cannula.

7. The method of claim 6, further comprising coupling the cannula and the plunger member to a handle assembly adapted to advance the plunger member relative to the cannula.

8. The method of claim 5, further comprising coupling an elastomeric seal onto a distal tip of the plunger member prior to inserting the plunger member into the interior space of the cannula.

9. The method of claim 8, wherein inserting the plunger member into the interior space of the cannula includes forming a fluid tight seal between the elastomeric seal and the interior space of the cannula.

10. The method of claim 8, wherein the elastomeric seal is stored within a sterile package prior to coupling the elastomeric seal onto the distal tip of the plunger member.

11. The method of claim 10, wherein the sterile package includes a base portion connected to a lid portion by a hinge, the hinge biasing the lid portion away from the base portion into an open condition in the absence of applied force.

12. The method of claim 1, wherein positioning the cannula within the passageway of the loading member includes advancing the cannula until a proximal flange of the cannula contacts the loading member.

13. The method of claim 12, further comprising rotating a locking hub of the loading member so that extension members of the locking hub overlie the proximal flange of the cannula.

14. The method of claim 1, further comprising manually loading the bone graft into the container prior to coupling the container to the loading member.

15. The method of claim 1, wherein coupling the container to the loading member results in the longitudinal axis of the container is orthogonal to the longitudinal axis of the loading member.

16. The method of claim 1, wherein advancing the first amount of the bone graft from the container to the loading member includes advancing the first amount of the bone graft from the container into a holding area of the loading member that is spaced apart from the cannula.

17. The method of claim 16, wherein inserting the loading tool into the interior space of the loading member includes inserting the loading tool through the holding area.

18. The method of claim 16, wherein positioning the cannula within the passageway of the loading member includes positioning a distal open end of the cannula adjacent the holding area.

19. The method of claim 1, wherein the loading member includes at least one viewing slot that opens to the passageway within the loading member.

20. The method of claim 19, wherein the cannula includes at least one volume indicator visible through the at least one viewing slot when the cannula is positioned within the passageway of the loading member.

* * * * *